(12) United States Patent
Berezin et al.

(10) Patent No.: US 10,100,100 B2
(45) Date of Patent: Oct. 16, 2018

(54) METALLOTHIONEIN-DERIVED PEPTIDE FRAGMENTS

(71) Applicant: University of Tasmania, Hobart (AU)

(72) Inventors: Vladimir Berezin, Copenhagen N (DK); Elisabeth Bock, Charlottenlund (DK); Milena Penkowa, Copenhagen V (DK)

(73) Assignee: University of Tasmania, Hobart (AU)

( * ) Notice: Subject to any disclaimer, the term of this patent is extended or adjusted under 35 U.S.C. 154(b) by 0 days.

(21) Appl. No.: 15/377,059

(22) Filed: Dec. 13, 2016

(65) Prior Publication Data

US 2017/0226190 A1 Aug. 10, 2017

Related U.S. Application Data

(63) Continuation of application No. 14/086,233, filed on Nov. 21, 2013, now Pat. No. 9,518,089, which is a continuation of application No. 12/223,947, filed as application No. PCT/DK2007/000070 on Feb. 12, 2007, now Pat. No. 8,618,060.

(30) Foreign Application Priority Data

Feb. 14, 2006 (DK) ................................. 2006 00212

(51) Int. Cl.
*A61K 38/00* (2006.01)
*A61K 39/00* (2006.01)
*A61K 35/30* (2015.01)
*C07K 14/825* (2006.01)
*C07K 7/08* (2006.01)

(52) U.S. Cl.
CPC .............. *C07K 14/825* (2013.01); *C07K 7/08* (2013.01); *A61K 38/00* (2013.01)

(58) Field of Classification Search
CPC .................................................. C07K 14/825
See application file for complete search history.

(56) References Cited

U.S. PATENT DOCUMENTS

| | | | |
|---|---|---|---|
| 5,814,480 A | 9/1998 | Hillman | |
| 6,787,637 B1 | 9/2004 | Schenk | |
| 8,618,060 B2 | 12/2013 | Berezin | |

FOREIGN PATENT DOCUMENTS

| | | |
|---|---|---|
| EP | 1361274 A1 | 11/2003 |
| WO | WO 99/57142 A2 | 11/1999 |
| WO | WO 00/38654 A1 | 7/2000 |
| WO | WO 03/105910 A1 | 12/2003 |
| WO | WO 2005/072270 A2 | 8/2005 |
| WO | WO 2005/123759 A2 | 12/2005 |

OTHER PUBLICATIONS

Ambjorn et al. "Metallothionein and a peptide modeled after metallothionein, EmtinB, induce neuronal differentiation and survival through binding to receptors of the low-density lipoprotein receptor family," J. Neurochemistry, vol. 104, pp. 21-37, (2008).

Ebadi et al. "Metallothionein-mediated neuroprotection in genetically engineered mouse models of Parkinson's disease," Molecular Brain Research, vol. 134, pp. 67-75, (2005).

Giralt et al. "Metallothionein-1+2 Protect the CNS after a Focal Brain Injury," Experimental Neurology, vol. 173, pp. 114-128, (2002).

Hasler et al. "Metal-Thiolate Clusters in the C-Terminal Domain of Human Neuronal Growth Inhibitory Factor (GIF)," Biochemistry, vol. 37, No. 42, pp. 14966-14973, (1998).

Hidalgo et al. "Roles of the metallothionein family of proteins in the central nervous system," Brain Research Bulletin, vol. 55, No. 2, pp. 133-145, (2001).

Hussain et al. "Role of Metallothionein and other Antioxidants in Scavenging Superoxide Radicals and their possible Role in Neuroprotection," Neurochem. Int., vol. 29, No. 2, pp. 145-152, (1996).

Irie et al. "Anti-amyloid β activity of metallothionein-III is different from its neuronal growth inhibitory activity: structure-activity studies," Brain Research, vol. 960, pp. 228-234, (2003).

Kiningham et al. "Neuronal Localization of Metallothioneins in Rat and Human Spinal Cord," Neurochem. Int. vol. 27, No. 1, pp. 105-109, (1995).

Klassen et al. "Megalin mediates renal uptake of heavy metal metallothionein complexes," Am J Physiology Renal Physiology, vol. 287, pp. F393-F403, (2004).

Kohler et al. "The role of metallothionein II in neuronal differentiation and survival," Brain Research, vol. 992, pp. 128-136, (2003).

May et al. "Molecular mechanisms of lipoprotein receptor signalling," Cellular and Molecular Life Sciences, vol. 62, pp. 2325-2338, (2005).

Miles et al. "Induction, Regulation, Degradation, and Biological Significance of Mammalian Metallothioneins," Critical Reviews in Biochemistry and Molecular Biology, vol. 35, No. 1, pp. 35-70, (2000).

Molony et al. "Hydroxylation of Lys Residues Reduces their Susceptibility to Digestion by Trypsin and Lysyl Endopeptidase," Analytical Biochemistry, vol. 258, pp. 136-137, (1998).

Ngo et al. "Computational Complexity Protein Structure Prediction, and the Levinthal Paradox," The Protein Folding Problem and Tertiary Structure Predication, pp. 491-495, (1994).

Okada et al. "Amino Acids and Peptides. XIII.," Chem. Pharm. Bull., vol. 34, No. 3, pp. 986-998, (1986).

Penkowa et al. "Disruption of the Blood-Brain Interface in Neonatal Rat Neocortex Induces a Transient Expression of Metallothionein in Reactive Astrocytes," GLIA, vol. 13, pp. 217-227, (1995).

Penkowa et al. "Impaired Inflammatory Response and Increased Oxidative Stress and Neurodegeneration After Brain Injury in Interleukin-6-Deficient Mice," GLIA, vol. 32, pp. 271-285, (2000).

(Continued)

*Primary Examiner* — Olga N Chernyshev
(74) *Attorney, Agent, or Firm* — Posternak Blankstein & Lund LLP

(57) ABSTRACT

The present invention relates to neural cell survival, differentiation and proliferation promoting peptide fragments derived from metallothioneins (MT), pharmaceutical compositions comprising said peptide fragments and uses thereof for treatment of diseases and conditions where the effects of stimulating neural cell proliferation, differentiation and/or survival, and/or stimulating neural plasticity associated with learning and memory are beneficial for treatment.

15 Claims, 14 Drawing Sheets
Specification includes a Sequence Listing.

(56) References Cited

OTHER PUBLICATIONS

Penkowa et al. "Metallothionein I+II Expression and Their Role in Experimental Autoimmune Encephalomyelitis," GLIA, vol. 32, pp. 247-263 (2000).

Penkowa et al. "Zinc or Copper Deficiency-Induced Impaired Inflammatory Response to Brain Trauma May Be Caused by the Concomitant Metallothionein Changes," Journal of Neurotrauma, vol. 18, No. 4, pp. 447-464, (2001).

Penkowa "Metallothionein Expression and Roles in the Central Nervous System," Biomedical Reviews, vol. 13, pp. 1-15, (2002).

Ronn et al. "A simple procedure for quantification of neurite outgrowth based on stereological principles," Journal of Neuroscience Methods, vol. 100, pp. 25-32, (2000).

Tang et al. "Measurement of Cadmium-Induced Metallothionein in Urine by ELISA and Prevention of Overestimation Due to Polymerization," J. Anal. Toxicol., vol. 23, pp. 153-158, (1999).

Tokuriki et al. "Stability effects of mutations and protein evolvability," Current Opinion in Structural Biology, vol. 29, pp. 596-604, (2009).

Trojan et al. "Immunoglobulin framework-derived peptides function as cytotoxic T-cell epitopes commonly expressed in B-cell malignancies," Nature Medicine, vol. 6, No. 6, pp. 667-672, (2000).

Uchida et al. "The N-terminal Portion of Growth Inhibitory Factor is Sufficient for Biological Activity," The Journal of Biological Chemistry, vol. 270, No. 7, pp. 3365-3369, (1995).

Vasak "Advances in metallothionein structure and functions," Journal of Trace Elements in Medicine and Biology, vol. 19, pp. 13-17, (2005).

Wells "Additivity of Mutational Effects in Proteins," Biochemistry, vol. 29, No. 37, pp. 8509-8517, (1990).

Willnow et al. "Defective forebrain development in mice lacking gp330/megalin," Proc. Natl. Acad. Sci. USA, vol. 96, pp. 8460-8464, (1996).

Zambenedetti et al. "Metallothioneins are highly expressed in astrocytes and microcapillaries in Alzheimer's disease," Journal of Chemical Neuroanatomy, vol. 15, pp. 21-26, (1998).

Zou et al. "Linking Receptor-mediated Endocytosis and Cell Signaling," The Journal of Biological Chemistry, vol. 279, No. 33, pp. 34302-34310, (2004).

METALLOTHIONEIN-DERIVED PEPTIDE FRAGMENTS

FIELD OF INVENTION

The present invention relates to neural cell survival, differentiation and proliferation promoting peptide fragments derived from metallothioneins (MT), pharmaceutical compositions comprising said peptide fragments and uses thereof for treatment of diseases and conditions where the effects of stimulating neural cell proliferation, differentiation and/or survival, and/or stimulating neural plasticity associated with learning and memory are beneficial for treatment.

BACKGROUND OF INVENTION

Metallothioneins (MTs) are a class of ubiquitously occurring low molecular weight cysteine- and metal-rich proteins containing sulfur-based metal clusters. The conservation of these clusters in an increasing number of three-dimensional structures of invertebrate, vertebrate and bacterial MTs signifies the importance of this structural motif. It is becoming increasingly clear that mammalian MTs have diverse functions including involvement in zinc homeostasis, protection against heavy metal toxicity and oxidative damage (Vasak et al., 2005). Mammalian MTs are single chain polypeptides of 61, 60 or 68 amino acid residues with an N-terminal acetylmethionine and often alanine at the carboxyl terminus. They contain 20 cysteine residues, which are central to the binding of metals. MTs have characteristic C-X-C, C-Y-C, and C-C sequences, where X and Y are non-cysteine amino acids. There are 7 bivalent ions for every 20 cysteines forming metal thiolate complexes (7-10 g atoms of metal per mol MT in a two domain structure (Hussain et al., 1996).

There are four MT subgroups, namely MT1, MT2, MT3, and MT4. The MT1 and MT2 isoforms, which differ by only a single negative charge, are the most widely expressed isoforms in different tissues. Human MT genes are clustered at a single locus on chromosome 16, and at least 14 of the 17 genes so far identified, are functional. These encode multiple isoforms of MT1 (MT1A, B, E, F, G, H, I, K, L and X), MT2, MT3 and MT4 (Miles et al., 2000).

Stimuli that can induce MT expression are metals. hormones (e.g. glucocorticoids), cytokines, a variety of other chemicals, inflammation, and stress. MT degradation takes place mainly in the lysosomes. MT appears less susceptible to proteolysis in the metal bound state. In vivo, metal-MTs have far longer half-lives than apo-MT (Miles et al., 2000).

MT1 and MT2 are present throughout the brain and spinal cord, and that the main cell type expressing these MT isoforms is the astrocyte; nevertheless, MT1 and MT2 expression was also found in ependymal cells, epithelial cells of choroid plexus, meningeal cells of the pia mater, and endothelial cells of blood vessels (Hidalgo et al., 2001).

MTs are stress-inducible proteins that maintain metal homeostasis and scavenge free radicals. It is generally accepted that the major functions of MTs are related to metal metabolism. Postulated functions include detoxification and storage of heavy metals and the regulation of cellular copper and zinc metabolism in response to dietary and physiological changes. Because astrocytes, as well as ependymal cells, richly express MTs, an attractive hypothesis is that both cell types serve to protect the CNS from metals transported parenchymally from the blood or the cerebrospinal fluid. In AD subjects cerebral white matter contains numerous MT1- and MT2-expressing astrocytes with an intense immunoreactivity of the cell body (Zambenedetti et al., 1998). Chronic inflammation has been postulated raising the possibility that the etiology of AD has an immunological component. Cytokines and interleukin (IL)-1, for instance, elevated in AD, induce MT1 and MT2 production in astrocytes suggesting that these proteins may have a relevant role in providing long-term protection against oxidative damage, injury and inflammation with a multiple compensatory mechanism involving the osmotic regulation of some metal ions. Clear-cut effects of CNS injury on MT1 and MT2 expression were investigated. These studies have shown a dramatic induction of these MT isoforms in response to kainic acid-induced seizures, cryogenic injury, ischaemia, and after treatment with 6-aminonicotinamide (Penkowa et al., 1995; 2000; 2001). MT1 and MT2 are significant inhibitors of apoptotic cell death in the CNS (Giralt et al., 2002). MT1 and MT2 deficient mice showed both increased oxidative stress and neuronal apoptosis during epileptic seizures, experimental autoimmune encephalomyelitis (EAE), and following traumatic brain injury. Likewise, transgenic MT1 overexpressing mice showed significantly reduced oxidative tissue damage and cell death during traumatic brain injury, focal cerebral ischemia, and 6-aminonicotinamide (6-AN)-induced brain stem toxicity. Furthermore, MT1 and MT21 improve the clinical outcome and reduce mortality in different CNS disorders (Penkowa, 2002). MT has recently been shown to mediate neuroprotection in genetically engineered mouse model of Parkinson's disease (Ebadi et al., 2005).

MT2 treatment has recently been shown to significantly stimulate neurite extension from both dopaminergic and hippocampal neurons. Moreover, MT2 treatment significantly increases survival of dopaminergic neurons exposed to 6-hydroxydopamine (6-OHDA) and protects significantly hippocampal neurons from amyloid β-peptide-induced neurotoxicity (Køhler et al., 2003). Treatment using MT2 and other MTs has been suggested for motor neuron disease, head injury, Alzheimer's and Parkinson's diseases (WO03105910). The molecular mechanisms of neuritogenic and neuroprotective actions of MTs are so far unknown.

Recently, it has been shown that MT1 binds to low-density lipoprotein receptor related protein 2 (LRP2)/megalin and the corresponding binding site in MT1 has been identified (Klassen et al., 2004).

Megalin/LRP2 is a scavenger receptor due to its multi-functional binding properties. Among its ligands are lipoproteins, vitamin-binding and carrier proteins, drugs, hormones and enzymes as well as signalling molecules. The intracellular domain of megalin interacts with signalling adaptor molecules which has been shown to be involved in regulation of edocytosis (see for review May et al, 2005). However, it remains to be uncertain, whether megalin participates directly in cellular signalling cascades by transducing extracellular signals to intracellular binding partners.

One of the best-characterized physiological functions of megalin is the proximal-tubular reuptake of low-molecular weight proteins (Zou et al., 2004). Another permanent feature is that megalin is required for a proper forebrain development: megalin knock-out mice demonstrate holoprosencephaly (Willnow et al., 1996).

REFERENCES

Vasak M. Advances in metallothionein structure and functions. J Trace Elem Med Biol. 2005, 19:13-17.

Giralt M, Penkowa M, Lago N, Camats J, Hernandez J, Molinero A and Hidalgo J. Metallothionein-1+2 protect the CNS after a focal brain injury. Exp. Neurol. 2002, 173 pp: 114-128.

Ebadi M, Brown-Borg H, El Refaev H, Singh B B, Garret S, Shavali S and Sharma S K. Metallothionein-mediated neuroprotection in genetically engineered mouse models of Parkinson's disease. 2005, 134:67-75.

Hidalgo H, Aschner M, Zatta P, and Vasak M. Roles of the metallothionein family of proteins in the central nervous system. Brain Res Bull. 2001, 55:133-145.

Hussain S, Slikker W, and Ali S F. Role of metallothioneins and other antioxidants in scavenging superoxide eadicals and their possible role in neuroprotection, Neurochem. Int. 1996, 29:145-152.

Klassen R B, Crenshaw K, Kozyraki R, Verroust P J, Tio L, Atrian S, Allen P L, Hammond T G Megalin mediates renal uptake of heavy metal metallothionein complexes. Am J Physiol Renal Physiol. 2004, 287:F393-403.

Køhler L B, Berezin V, Bock E and Penkowa M. The role of metallothionein II in neuronal differentiation and survival. Brain Res. 2003, 992:128-136.

May P, Herz J, Bock H H. 2005 Molecular mechanisms of lipoprotein receptor signalling. Cell Moll Life Sci. 62:2325-2338.

Miles A T, Hawksworth G M, Beattie J H, Rodilla V. Induction, regulation, degradation, and biological significance of mammalian metallothioneins. Crit Rev Biochem Mol Biol. 2000, 35:35-70.

Penkowa M and Moos T. Disruption of the blood-brain interface in neonatal rat neocortex induces a transient expression of metallothionein in reactive astrocytes. Glia 1995, 13:217-227.

Penkowa M and Hidalgo J, Metallothionein I+II expression and their role in experimental encephalomyelitis. Glia 2000, 32:247-263.

Penkowa M, Giralt M, Carrasco J, Hadberg H and Hidalgo H. Impaired inflammatory response and increased oxidative stress and neurodegeneration after brain injury in interleukin-6-deficient mice. Glia 2000, 32:271-285.

Penkowa M Giralt M, Thomsen P, Carrasco J and Hidalgo J. The zinc or copper deficiency-induced impaired inflammatory response to brain trauma may be caused by the concomitant metallothionein changes. J. Neurotrauma 2001, 18:447-463.

Penkowa M. Metallothionein expression and roles in the central nervous system. Biomed. Rev. 2002, 13:1-18.

Rønn L C, Ralets I, Hartz B P, Morten B, Berezin A, Berezin V, Møller A, and Bock E. A simple procedure for quantification of meurite outgrowth based on stereological principles. J. Neurosci. Meth. 2000, 100:25-32.

Tang W, Kido T, Gross W A, Nogawa K, Sabbioni E and Shaikh Z A. Measurement of cadmium-induce metallothionein in urine by ELISA and prevention of overestimation due to polymerization. J. Anal. Toxicol. 1999, 23:153-158.

Willnow T E, Hilpert J, Armstrong S A, Rohlmann A, Hammer A E, Burns D K, et al. 1996. Defective forebrain development in mice lackin gp339/megalin. Proc Natl Acad Sci USA 93:8460-8464.

Zambenedetti P, Giordano R and Zatta P. Metallothioneins are highly expressed in astrocytes and microcapillaries in Alzheimer's disease. J. Chem. Neuroanat. 1998, 15:21-26.

Zou Z, Chung B, Nguyen T, Mentone S, Thompson B, and Biemesderfer D. 2004 Linking receptor-mediated endocytosis and cell signalling: evidence for regulated intramembrane proteolysis of megalin in proximal tubule. J Biol Chem 179:34302-34310.

SUMMARY OF THE INVENTION

The present invention relates to short peptide sequences capable of stimulating neuronal cell differentiation, neuronal cell survival and neural plasticity associated with learning and memory, capable of inhibiting the oxidative stress and inflammatory responses, modulating of survival and neuroprotection, promoting the effects of growth factors and regulatory molecules and their receptors.

According to one aspect of the invention, the peptide sequences described herein comprise a common structural motif which is essential for biological activity of peptides.

Such peptides according to the invention comprise a sequence of at most 25 contiguous amino acid residues which comprise an amino acid motif of the formula: S/D/E-$(x)_n$-S/D/E-K/S, wherein $(x)_n$ is a sequence of any amino acid residues with an integer n from 4 to 6.

A peptide as above is according to the invention homologous to a subsequence of a protein of the metallothionein family, a metallothionein (MT), wherein said subsequence is a functional domain of MT involved in stimulation of neurite outgrowth, neural cells survival, neural plasticity associated with learning and memory and/or inhibition of oxidative stress, inflammatory responses by MT, and it is also involved in homodimerization (homophylic binding) of metallothioneins. Accordingly, a peptide sequence comprising the amino acid motif of the invention is not only a structural homologue the latter MT functional domain, but as well a functional homologue of MT protein or a peptide fragment of MT derived from MT functional domain involved in execution of the mentioned functions of MT.

Accordingly, the invention in another aspect relates to a peptide fragment of MT capable of mimicking biological function of MT, for example capable of stimulating neurite outgrowth, neuronal survival, neural plasticity associated with learning and memory and/or inhibiting inflammation. Still, in another aspect, the invention relates to a fragment of MT which is capable of modulating of biological function of MT by stimulating or inhibiting homophylic binding of MT or by stimulating or inhibiting MT binding to its receptor.

The invention also relates to a compound comprising a peptide sequence comprising the motif of the invention and/or peptide fragment of MT.

Further aspects of the invention relate to use of a peptide sequence of the invention as a medicament or for the manufacturing of a medicament, said medicament is for treatment a condition involving stimulating neurite outgrowth, neural cell survival, neural cell plasticity associated with learning and memory and/or inhibiting inflammation;

pharmaceutical composition comprising a peptide sequence of the invention or compound comprising thereof;

antibody capable of binding to an epitope comprising a peptide sequence of the invention;

pharmaceutical composition comprising an antibody of the invention;

methods of treatment involving using peptide sequences, compounds, medicaments, antibodies of the invention or pharmaceutical compositions comprising thereof.

DETAILED DESCRIPTION OF THE INVENTION

1. Peptide

Figure 1:
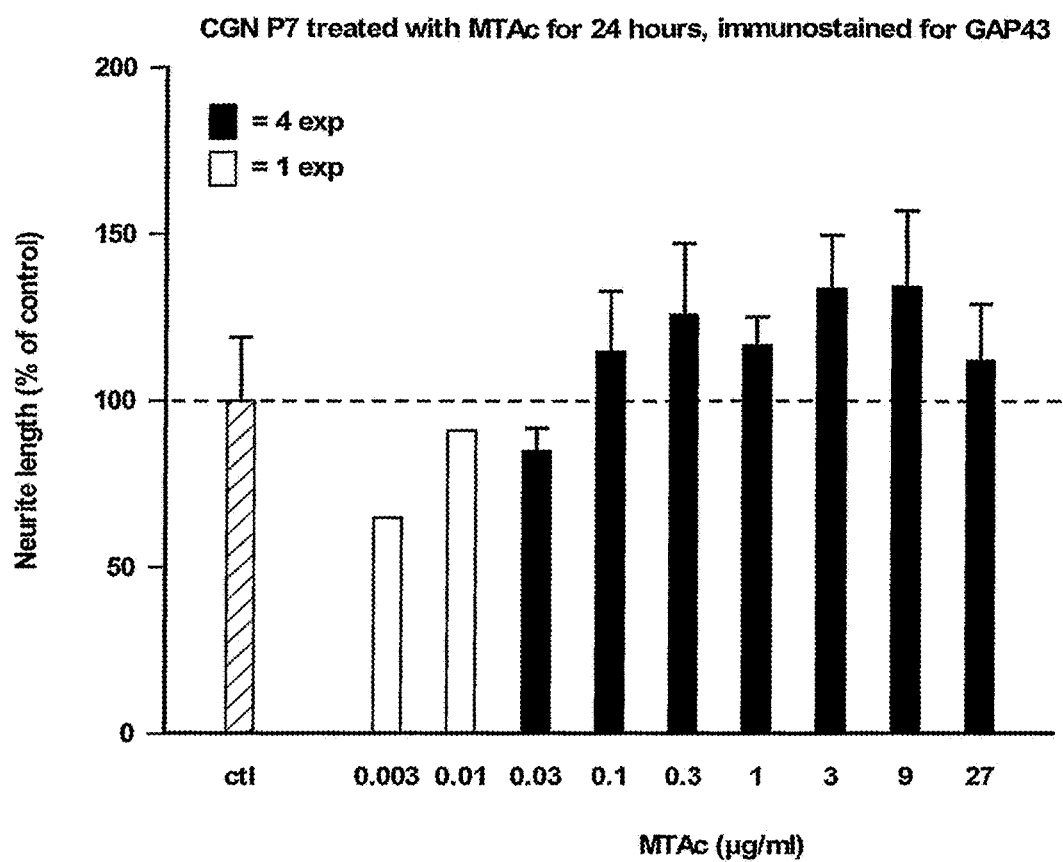
FIG. 1 Effect of the MTAc peptide on neurite outgrowth
FIG. 2 Effect of the MTBc peptide on neurite outgrowth.
Figure 2:
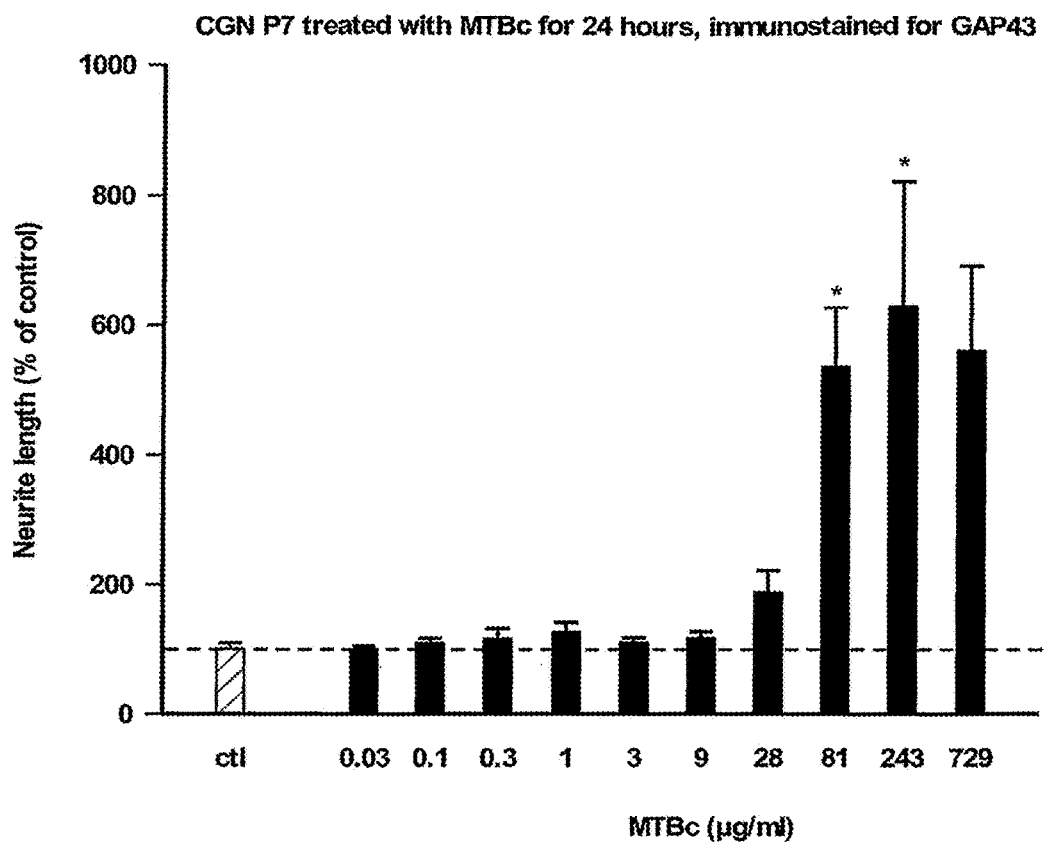
Figure 3:
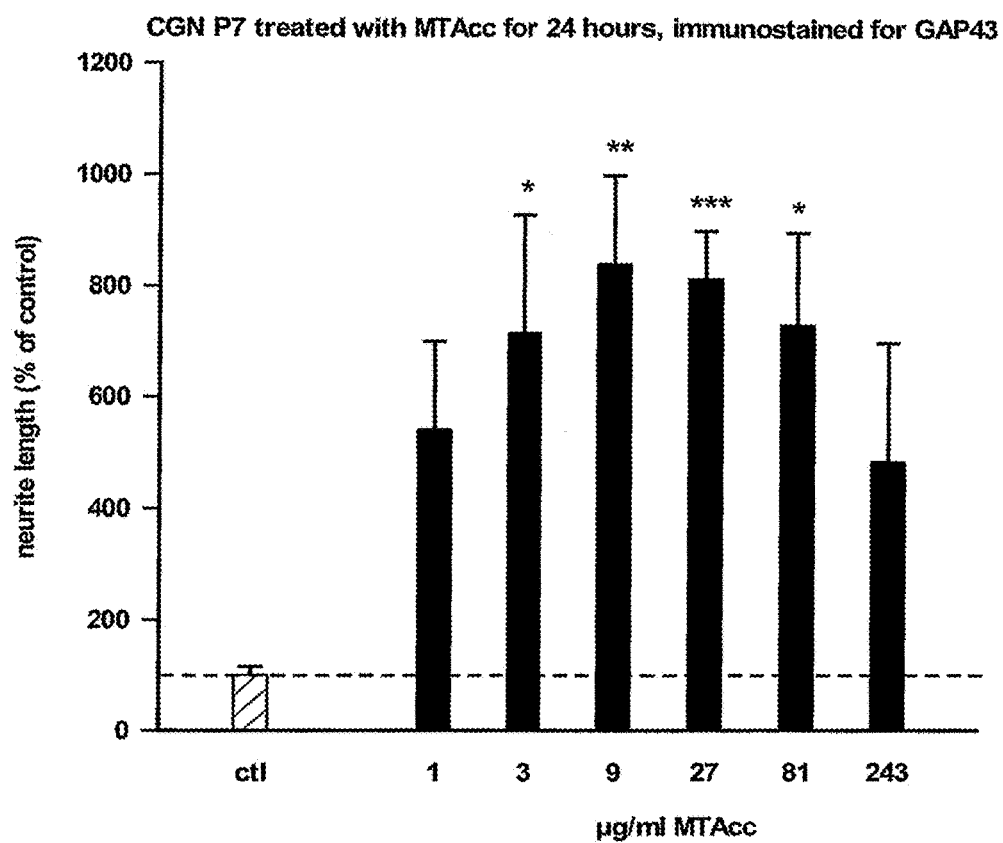
FIG. 3 Effect of the MTAcc peptide on neurite outgrowth.
Figure 4:
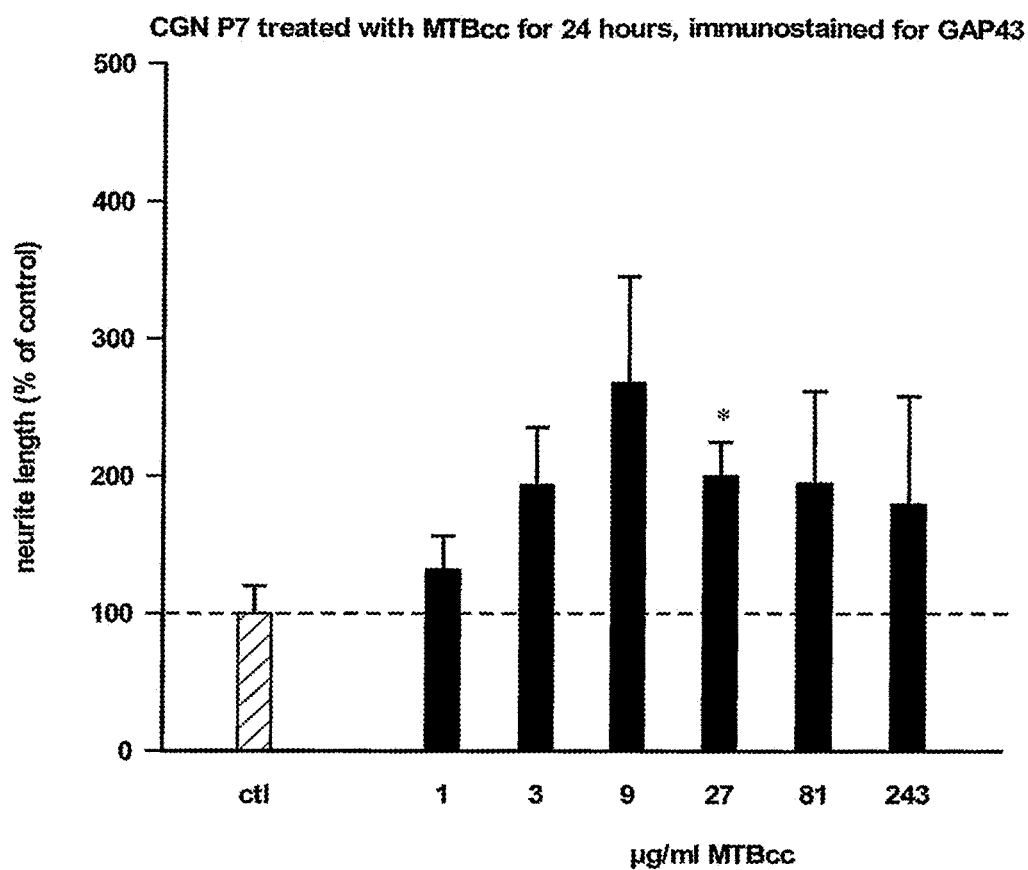
FIG. 4 Effect of the MTBcc peptide on neurite outgrowth.
Figure 5:
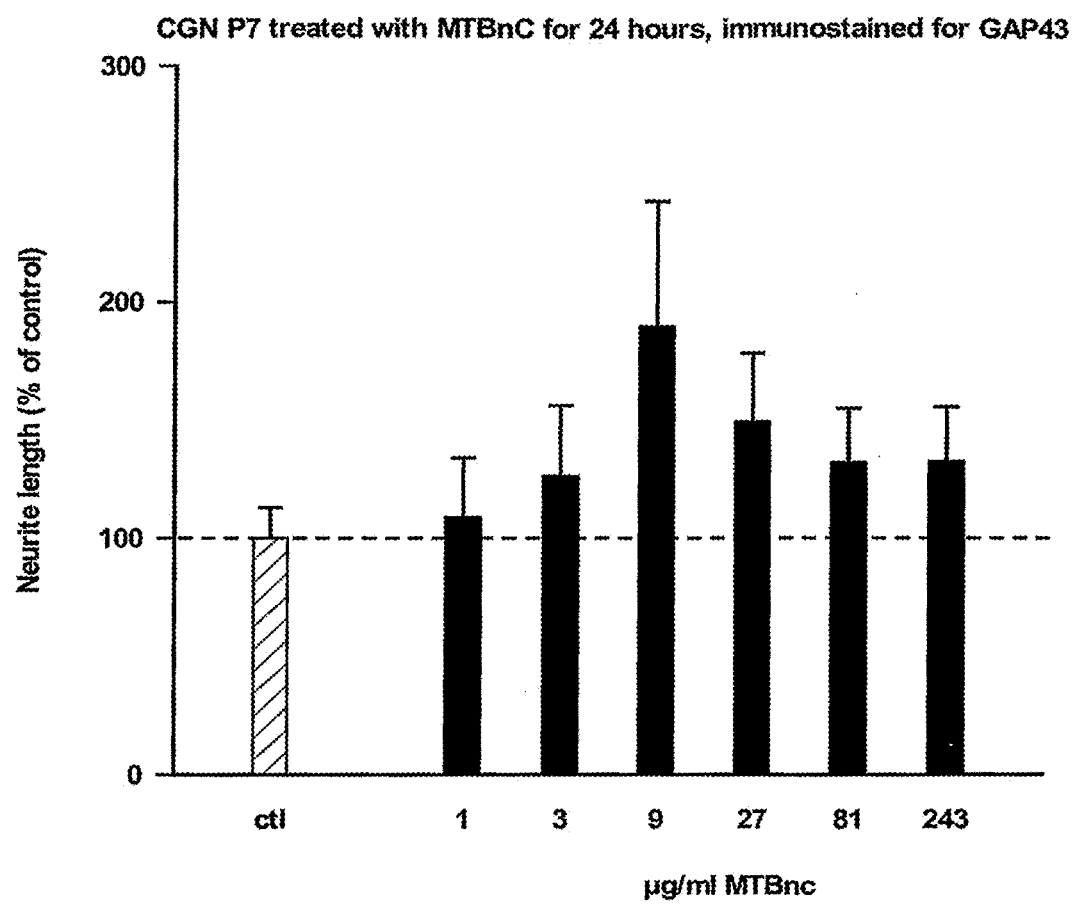
FIG. 5 Effect of the MTBnc peptide on neurite outgrowth.
Figure 6:
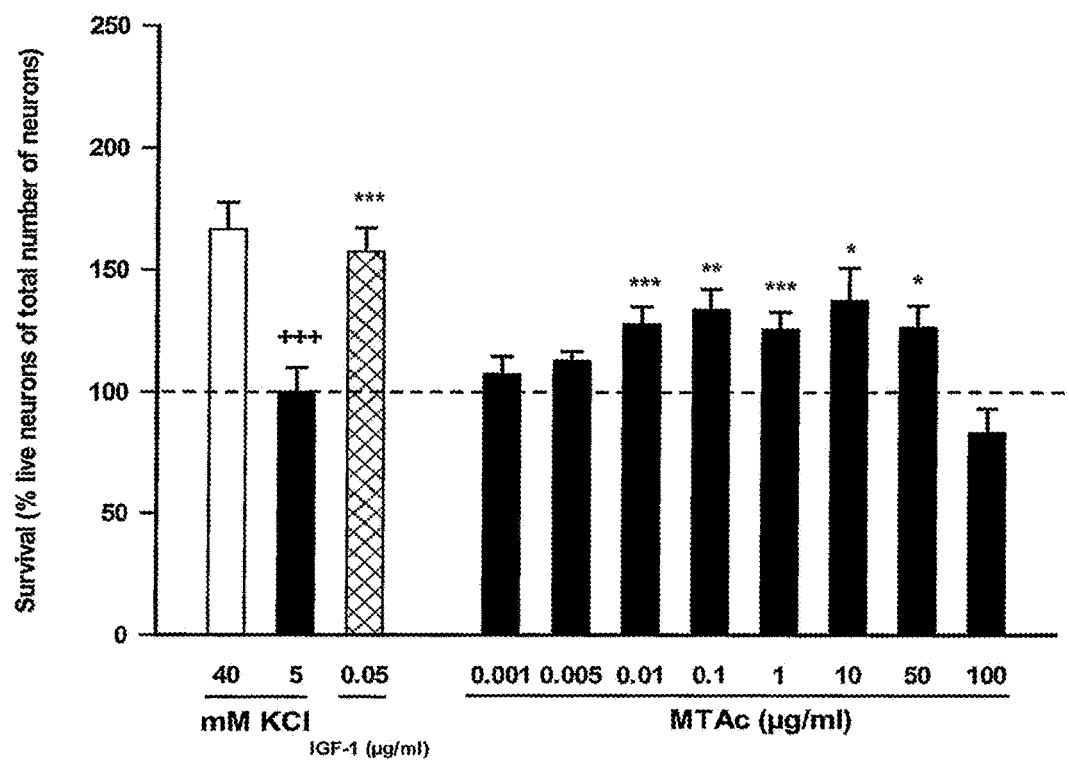
FIG. 6 Effect of the MTAc peptide on neuronal survival.
Figure 7:
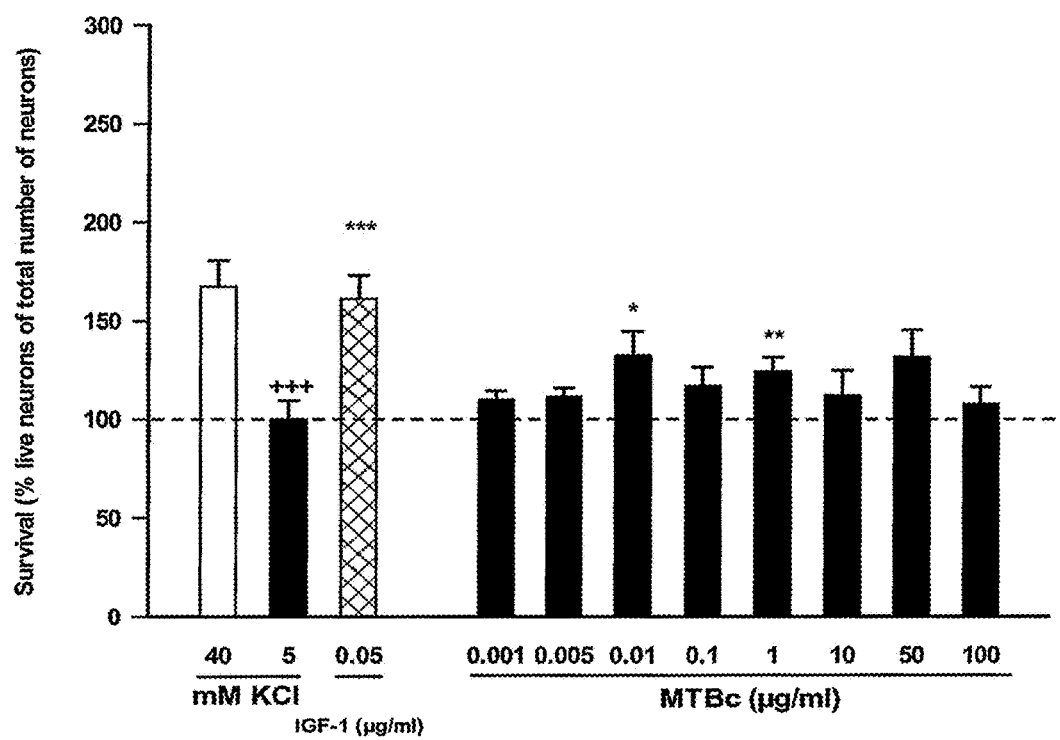
FIG. 7 Effect of the MTBc peptide on neuronal survival.
Figure 8:
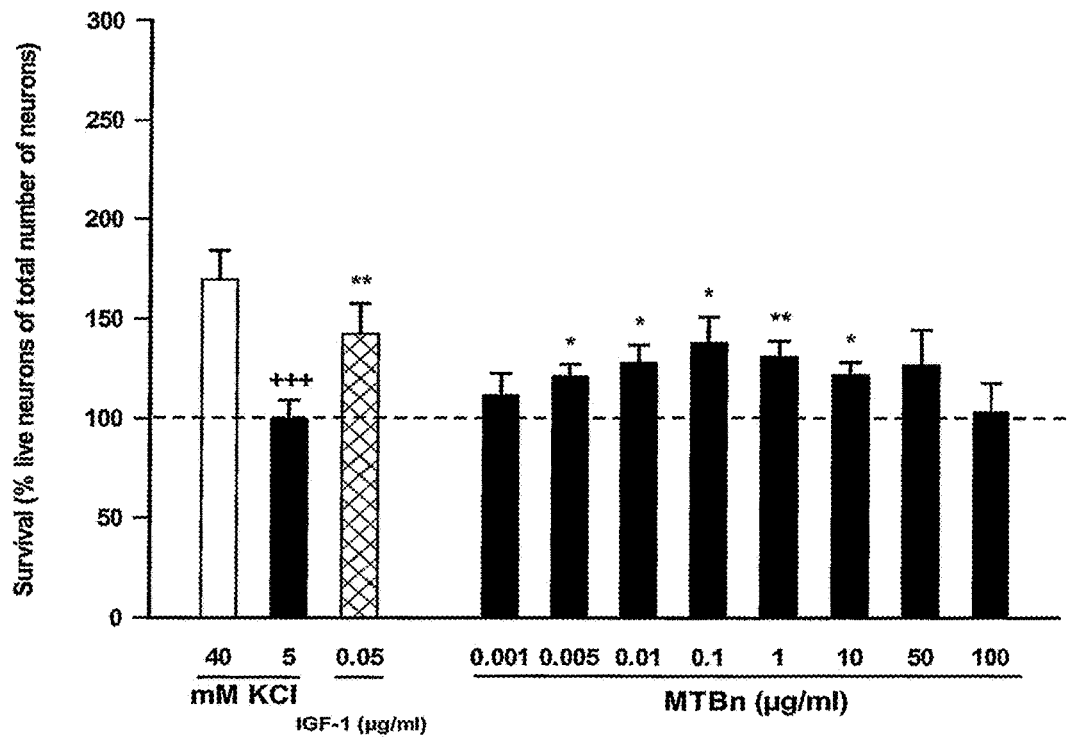
FIG. 8 Effect of the MTBn peptide on neuronal survival.
Figure 9:
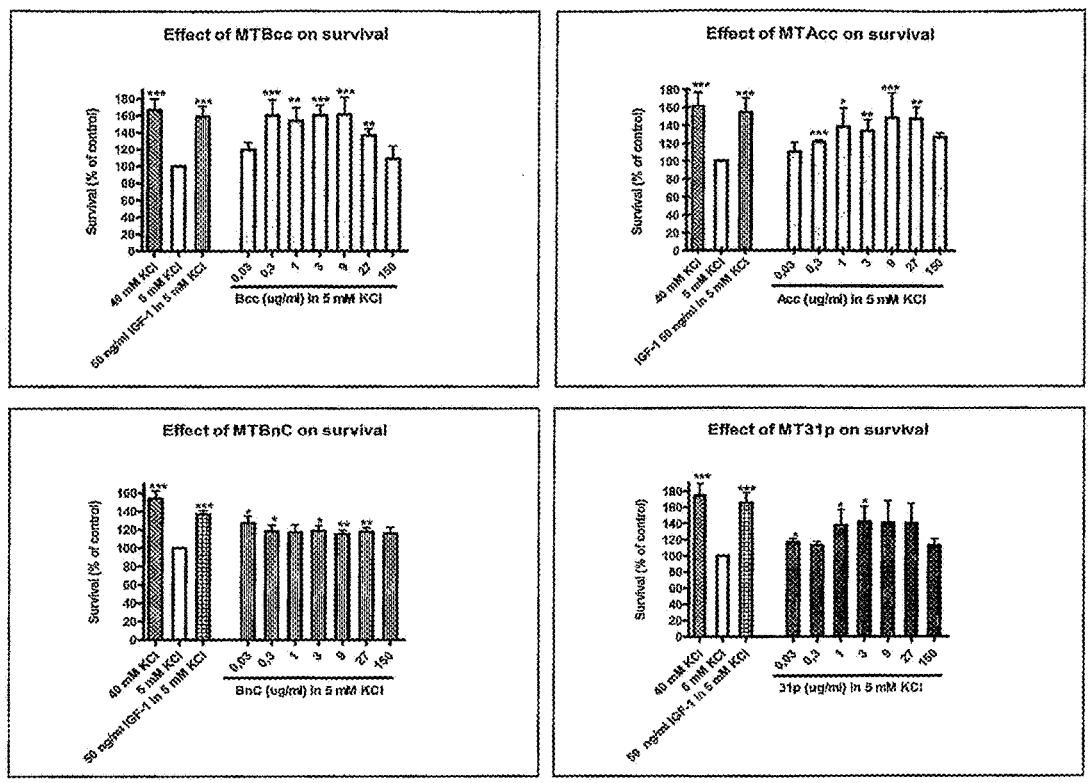
FIG. 9 Effect of the MTBcc, MTAcc, MTBnc and MT31p peptides on neuronal survival.

In a first aspect the present invention relates to a peptide comprising of at most 25 contiguous amino acid residues comprising an amino acid motif of the formula: S/D/E-(x)$_n$-S/D/E-K/S, wherein (x)$_n$ is a sequence of any amino acid residues with an integer n from 4 to 6.

In one embodiment, (x)n is an amino acid sequence wherein n is 4, in another embodiment n is 6. The amino acid sequence (x)n is a sequence of any amino residues, however, in some preferred embodiments it may comprise at least one of the following amino acid residues: K, S, E or C.

The invention preferably relates to peptide sequences comprising amino acid residues in the range of 8-25 amino acid residues, such as from 9 to 25 amino acid residues, for example from 10 to 25 amino acid residues. In some embodiments the peptide sequence may be between 11 and 25 amino acid residues, such as between 12 and 25, for example from 13 to 25 amino acid residues. In other embodiments the amino acid sequence may comprise about 15 amino acid residues, such as 14 or 16 amino acid residues, or it may be about 20 amino acid residues in length, such as from 17 to 19 amino acid residues, or it may comprise from 20 to 25 amino acid residues. A short amino acid sequence comprising at most 20 contiguous amino acid residues is preferred, however, the invention includes in the scope amino acid sequences which may comprise about 23 or 25 amino acid residues, such as 21, 22, 23, 24, 25 or 26 amino acid residues, or may be about 30 amino acid residues, such as 27, 28 or 29 amino acid residues, or be about 35 amino acid residues, such as from 31 to 34 amino acid residues.

A peptide comprising the motif of the invention, may comprise in some embodiments at least one amino acid residue G within a sequence of 10 amino acid residues comprising the motif, preferably, amino acid residue G precedes the amino acid residue S/D/E at any corresponding position of the motif.

The invention also relates to a peptide as above wherein the amino acid residue S/D/E at any position of the motif is substituted for amino acid residue C.

A peptide as above may for example comprise or consist of an amino acid sequence selected from the following sequences:

KKSSCSCSPVGSAK (SEQ ID NO: 1)

AQGSISKGASDKSS (SEQ ID NO: 2)

MDPNSSSAAGDSST (SEQ ID NO: 3)

SAGSSKSKESKSTS (SEQ ID NO: 4)

AQGSICKGASDKSS (SEQ ID NO: 5)

MDPNCSCAAGDSST (SEQ ID NO: 6)

SAGSCKCKESKSTS (SEQ ID NO: 7)

KGGEAAEAEAEK, (SEQ ID NO: 8)

or be a fragment, or a variant of any of these sequences.

According to the invention a peptide comprising a sequence selected from SEQ ID NOS: 1-8 is homologous to a subsequence of a metallothionein selected from the group consisting of metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-1I (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) and metallothionein-4 (MT4). The sequences of the latter mentioned metallothioneins are identified in the Gene Bank under the following Acc. Nos: Q9BQN2, P04731, P07438, P04732, P04733, P13640, P80294, P80295, P80296, Q93083, P80297, P02795, P25713, P47944, respectively.

More particular, a peptide comprising a sequence selected from SEQ ID NOs: 1-8 is homologous to a subsequence of MT which comprises one of the following amino acid sequences:

KKSCCSCCPMSCAK (SEQ ID NO: 9)

KKCCCSCCPVGCAK (SEQ ID NO: 10)

-continued

KKSCCSCCPVGCAK (SEQ ID NO: 11)

KKSCCSCCPVGCSK (SEQ ID NO: 12)

KKSCCSCCPVGCAK (SEQ ID NO: 13)

KKSCCSCCPLGCAK (SEQ ID NO: 14)

KKSCCSCCPVGCAK (SEQ ID NO: 15)

KKSCCSCCPVGCAK (SEQ ID NO: 16)

KKSCCSCCPVGCAK (SEQ ID NO: 17)

KKSCCSCCPMGCAK (SEQ ID NO: 18)

KKSCCSCCPVGCAK (SEQ ID NO: 19)

KKSCCSCCPVGCAK (SEQ ID NO: 20)

KKSCCSCCPAECEK (SEQ ID NO: 21)

RKSCCPCCPPGCAK (SEQ ID NO: 22)

AQGCICKGASEKCS (SEQ ID NO: 23)

AQGCVCKGSSEKCS (SEQ ID NO: 24)

AQGCVCKGASEKCS (SEQ ID NO: 25)

AQGCVCKGASEKCS (SEQ ID NO: 26)

AQGCICKGASEKCS (SEQ ID NO: 27)

AQGCICKGASEKCS (SEQ ID NO: 28)

AQGCICKGASEKCS (SEQ ID NO: 29)

AQGCICKGASEKCS (SEQ ID NO: 30)

AQGCICKGTSDKCS (SEQ ID NO: 31)

AQGCVCKGASEKCS (SEQ ID NO: 32)

AQGCICKGTSDKCS (SEQ ID NO: 33)

AQGCICKGASDKCS (SEQ ID NO: 34)

AKDCVCKGGEAAEAEAEKCS (SEQ ID NO: 35)

ARGCICKGGSDKCS (SEQ ID NO: 36)

MDPNCSCATGGSCT (SEQ ID NO: 37)

MDPNCSCTTGGSCA (SEQ ID NO: 38)

MDPNCSCATGGSCT (SEQ ID NO: 39)

MDPNCSCAAGVSCT (SEQ ID NO: 40)

MDPNCSCAAGVSCT (SEQ ID NO: 41)

MDPNCSCEAGGSCA (SEQ ID NO: 42)

MDPNCSCAAGVSCT (SEQ ID NO: 43)

MDPNCSCAAAGVSCT (SEQ ID NO: 44)

MDPNCSCSPVGSCA (SEQ ID NO: 45)

MDPNCSCATGGSCS (SEQ ID NO: 46)

MDPNCSCDPVGSCA (SEQ ID NO: 47)

MDPNCSCAAGDSCT (SEQ ID NO: 48)

MDPETCPCPSGGSCT (SEQ ID NO: 49)

MDPRECVCMSGGICM (SEQ ID NO: 50)

CTGSCKCKECKCNS (SEQ ID NO: 51)

CAGSCKCKECKCTS (SEQ ID NO: 52)

CAGSCKCKECKCTS (SEQ ID NO: 53)

CAGSCKCKECKCTS (SEQ ID NO: 54)

CASSCKCKECKCTS (SEQ ID NO: 55)

CAGSCKCKKCKCTS (SEQ ID NO: 56)

CAGSCKCKECKCTS (SEQ ID NO: 57)

CASSCKCKECKCTS (SEQ ID NO: 58)

CAGSCKCKECKCTS (SEQ ID NO: 59)

CASSCKCKECKCTS (SEQ ID NO: 60)

CAGSCKCKECKCTS (SEQ ID NO: 61)

CAGSCKCKECKCTS (SEQ ID NO: 62)

CADSCKCEGCKCTS (SEQ ID NO: 63)

CGDNCKCTTCNCKT. (SEQ ID NO: 64)

In different embodiments of the invention it may preferably be selected a peptide which is homologues to a specific subsequence of a selected group of subsequences. Accordingly, in one embodiment it may be a peptide which is homologues to a subsequence which is selected from the group of subsequences identified as SEQ ID NOs:9-22.

In another embodiment it may be a peptide which is homologous to a subsequence comprising an amino acid sequence selected from the group consisting of SEQ ID NOs:23-36.

In other embodiments it may be a peptide which is homologues to a subsequence which comprise an amino acid sequence selected from any of the sequences identified as SEQ ID NOs:37-50, or to a subsequence which comprise an amino acid sequence selected from any of the sequences identified as SEQ ID NOs: 51-64.

Still in other embodiments, a peptide may be homologues to a subsequence of a particular MT, for example to be homologous to a subsequence of MT1A, said subsequence is selected from SEQ ID NOs:9, 23, 37 or 51; or a subsequence of MT1B, said subsequence is selected from SEQ ID NOs:10, 24, 38 or 52. The following are other examples of preferred subsequences of particular MTs which are included in the scope of the invention:

MT1E subsequence selected from SEQ ID NOs:11, 25, 39 or 53;
MT1F subsequence selected from SEQ ID NOs:12, 26, 40 or 54;
MT1G subsequence selected from SEQ ID NOs:13, 27, 41 or 55;
MT1H subsequence selected from SEQ ID NOs:14, 28, 42 or 56;
MT1I subsequence selected from SEQ ID NOs:15, 29, 43 or 57;
MT1K subsequence selected from SEQ ID NOs:16, 30, 44 or 58;
MT1L subsequence selected from SEQ ID NOs:17, 31, 45 or 59;
MT1R subsequence selected from SEQ ID NOs:18, 32, 46 or 60;
MT1X subsequence selected from SEQ ID NOs:19, 33, 47 or 61;
MT2 subsequence selected from SEQ ID NOs:20, 34, 48 or 62;
MT3 subsequence selected from SEQ ID NOs:21, 35, 49 or 63;
MT4 subsequence selected from SEQ ID NOs:22, 36, 50 or 64.

Any of the subsequences of the MTs identified above may also be a part of an amino acid sequence of the peptide according to invention. Thus, a further aspect of the invention relates to a peptide comprising an amino acid sequence selected from SEQ ID NOs:9-64, or comprising a fragment or variant of said sequence, or consisting of any of these sequences, fragments or variants.

Sequence homology may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. The terms "sequence similarity" sequence identity" and "sequence homology" are used in the present application interchangeably when referred to a number or percentage of identical or similar amino acid residues in two collated amino acid sequences. "Similar amino acid residues" are amino acid residues derived from the same group of "conservative" amino acid residues. The latter groups are discussed further in the application.

In the present application the standard one-letter code for amino acid residues is applied as well as the standard three-letter code. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues, DAP, DAPA and 4Hyp.

Also, according to the invention modifications of the compounds/peptides may be performed, such as for example glycosylation and/or acetylation of the amino acids.

Basic amino acid residues are according to invention represented by the residues of amino acids Arg, Lys, and His, acidic amino acid residues—by the residues of amino acids Glu and Asp. Basic and acidic amino acid residues constitute a group of charged amino acid residues. The group of hydrophobic amino acid residues is represented by the residues of amino acids Leu, Ile, Val, Phe, Trp, Tyr, Met, Ala and Pro.

The invention relates to naturally occurring, synthetically/recombinant prepared peptide sequence/fragments, and/or peptide sequence/fragments prepared by means of enzymatic/chemical cleavage of a bigger polypeptide, wherein said peptide sequence/fragments are integral parts of said bigger polypeptides. The invention relates to isolated individual peptide sequences.

As it is mentioned above, the invention relates to variants of peptide sequences described in the application as well.

In one aspect the term "variant of a peptide sequence" means that the peptides may be modified, for example by substitution of one or more of the amino acid residues. Both L-amino acids and D-amino acids may be used. Other modification may comprise derivatives such as esters, sugars, etc. Examples are methyl and acetyl esters.

In another aspect "variants" may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

In still another aspect, variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one asparagine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:
P, A, G (neutral, weakly hydrophobic),
S, T (neutral, hydrophilic)
Q, N (hydrophilic, acid amine)
E, D (hydrophilic, acidic)
H, K, R (hydrophilic, basic)
L, I, V, M, F, Y, W (hydrophobic, aromatic)
C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions. In particular, a variant which may be an amino acid sequence having at least 60%, more preferably at least 70%, more preferably at least 80%, more preferably at least 90%, more preferably 95% homology to an amino acid sequence of the invention, such as a sequence comprising the motif of the invention, for example a sequence selected from SEQ ID NOs: 1-64, or may be an amino acid sequence having at least 60%, more preferably at least 70%, more preferably at least 80%, more preferably at least 90%, more preferably 95% positive amino acid matches compared to an amino acid sequence of the invention, such as a sequence comprising the motif of the invention, for example a sequence selected from SEQ ID NOs: 1-64. A positive amino acid match is defined herein as an identity or similarity defined by physical and/or chemical properties of the amino acids having the same position in two compared sequences. Preferred positive amino acid matches of the present invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences. The homology of the sequences as mentioned above may be routinely calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90;

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The following variants are preferred by the invention:
1. a variant which is an amino acid sequence of at least 6 amino acid residues having at least 65% sequence similarity with a sequence selected from the sequences of SEQ ID NOs:1-64, preferably an amino acid sequence of 6 to 20 contiguous amino acid residues, which has more then 70% sequence similarity with a sequence selected from the sequences of SEQ ID NOs:1-64, such as from 71% to 80% similarity, preferably from 81% to 85%, more preferably from 86% to 90%, even more preferably from 91% to 95%, and even more preferably more then 95% of sequence similarity.
2. a variant which consists of a sequence of SEQ ID NOs:1-64, said sequence comprising one or more modifications of amino acid residues, such as for example modification as discussed above.

As it is mentioned above, the present invention also relates to fragments of the peptide sequences described in the application.

A preferred fragment of the invention is a fragment of a sequence selected from SEQ ID NOs:1-64 which has the length of about 40% of the length of said sequence, more preferably at least 50%, more preferably at least 60%, more preferably at least 70%, more preferably at least 80%, more preferably at least 90%, more preferably at least 95%.

The invention relates to variants and fragments of above which have at least one functional activity of a sequence selected from SEQ ID NOs:1-64. Thus, preferred variants and fragments of the invention are functional equivalents/homologues of the amino acid sequences identified as SEQ ID NOs:1-64.

Thus, by the term "functional equivalent/homologue" in the present context is an amino acid sequence which has at least 65% of homology with a sequences selected from SEQ ID NOs:1-64 or a sequence which has at least 40% of the length of a sequence selected from SEQ ID NOs:1-64, and which is capable of at least one functional activity of the sequence which it has homology with, or which it is a fragment of, for example it is capable of stimulating neural plasticity, such as associated with neural cell differentiation and/or such as associated with memory and learning, capable of stimulating of cell survival, such as inhibiting apoptosis, capable of binding to a receptor and modulating activity of said receptor, or capable of inhibiting inflammation.

The invention relates both to naturally occurring, synthetically or recombinantly prepared peptides and peptides prepared by means of enzymatic/chemical cleavage of proteins. The peptides having the amino acid sequences corresponding to subsequences of bigger polypeptides, such as for example peptides comprising or consisting of subsequences of the MTs described above, to be understood are derived from the sequences of said bigger polypeptides or proteins. These peptides may be produced either by enzymatic cleavage of proteins or prepared by means of recombinant expression or chemical synthesis.

Thus, the invention further relates to fragment of a metallothionein, said fragment preferably is derived from a human metallothionein, more preferably from metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-1I (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) or metallothionein-4 (MT4). The invention relates to a fragment of metallothionein which is capable of stimulating neurite outgrowth, neuronal survival, activating a receptor, stimulating neural plasticity associated with learning and memory and/or inhibiting inflammation. In particular, the invention relates to fragments of the above mentioned metallothioneins which comprise or consist of a sequence selected from SEQ ID NOs:9-64 or a fragments of said sequence. In particular embodiments a peptide fragment which comprises or consists of a particular sequence of the described above may be preferred. The invention preferably relates to the fragments of metallothioneins which comprise at most 20 amino acids residues.

2. Compound

A compound may contain a single copy of an individual amino acid sequence selected from any of the described above, or it may contain two or more copies of such amino acid sequence. This means that compound of the invention may be formulated as a monomer of a peptide sequence, such as containing a single individual peptide sequence, or it may be formulated as a multimer of a peptide sequence, i.e containing two or more individual peptide sequences, wherein said individual peptide sequences may be represented by two or more copies of the same sequence or by two or more different individual peptide sequences. A multimer may also comprises a combination of the full-length sequence and one or more fragments thereof. In one embodiment a compound may contain two amino acid sequences, such compound is defined herein as dimer, in another embodiment a compound may contain more then two amino acid sequences, such for example three, four or more sequences. The present invention preferably relates to compounds containing two or four peptide sequences of the invention. However, compounds containing 3, 5, 6, 7, 8 or more sequences are also in the scope of the invention.

The compounds may be formulated as dimers or multimers comprising more then two copies of individual peptide fragments which may have the identical amino acid sequences or different amino acid sequences. One example of such compound may be a dimeric compound containing SEQ ID NO: 1 and SEQ ID NO: 2 or a dimeric compound containing SEQ ID NO: 1 and SEQ ID NO: 3. Any other combinations of the sequences of the invention may be made depending on different embodiments. The sequences may be connected to each other via peptide bond, or connected to each other through a linker molecule or grouping.

As already mentioned above, a compound of the invention may contain two or more copies of a single sequence, such as for example two copies of any of the sequences selected from SEQ ID NOs: 1-64, wherein said two sequences may be connected to each other via a linker molecule or grouping. A compound wherein the sequences are connected via a linker grouping is preferred. One example of such linking grouping may be an achiral di-, tri- or tetracarboxylic acid. Suitable achiral di-, tri- or tetracarboxylic acids and a method of production such a compound (a ligand presentation assembly method (LPA)) are described in WO0018791 and WO2005014623. Another example of a possible linker may be the amino acid lysine. Individual peptide sequences may be attached to a core molecule such as lysine forming thereby a dendritic multimer (dendrimer) of an individual peptide sequence(s). Production of dendrimers is also well known in the art (PCT/

US90/02039, Lu et al., (1991) Mol Immunol. 28:623-630; Defoort et al., (1992) Int J Pept Prot Res. 40:214-221; Drijfhout et al. (1991) Int J Pept Prot Res. 37:27-32), and dedrimers are at present widely used in research and in medical applications. It is a preferred embodiment of the invention to provide a dendrimeric compound comprising four individual amino acid sequences attached to the lysine core molecule. It is also preferred that at least one of the four individual amino acid sequences comprises an amino acid sequence of the formula defined above. It is even more preferred if the all four individual amino acid sequences of a dendrimeric compound individually comprise an amino acid sequence of the formula defined above.

Multimeric compounds of the invention, such as LPA-dimers or Lysin-dendrimers, are among preferred compounds of the invention. However, other types of multimeric compounds comprising two or more individual sequences of the invention may be preferred depending on the embodiments.

3. Biological Activity

A peptide sequence of the invention and a compound comprising a sequence of the invention possess biological activity. The invention preferably relates to a biological activity selected from capability of stem cell differentiation, for example by stimulating neuronal cell precursor differentiation;

capability of stimulating neural cell differentiation and/or regeneration of nerves, for example by stimulating neurite outgrowth;

capability of stimulating neural plasticity associated with memory and learning, for example by stimulating synaptic efficacy;

capability of stimulating of cell survival, in particular stimulating survival neuronal cells, for example by inhibiting apotosis of neural cells, capability of inhibiting the oxidative stress response, for example by stimulating expression of scavenges of reactive oxygen species capability to activate astrogliosis, such as capability of stimulating astrocytes to express neuroprotective growth factors and proteins such as e.g. BDNF, NT-3, GDNF, neurturin, artemin, NGF, variety of fibroblast growth factors (FGFs), S100-proteins (S100A4, S100A6, S100A10, S100A12, S100B), IGF-2, neuregulin;

capability of inhibiting inflammation, for example inhibiting the activation of microglia and macrophages, inhibiting expression of pro-inflammatory cytokines and/or by stimulating anti-inflammatory responses;

capability of stimulating angiogenesis in the lesioned area, for example by stimulating expression of growth factor promoting angiogenesis such as VEGF and FGF2.

capability of binding to a receptor, for example megalin receptor (Swiss-prot Ass. number: P98164) or MT protein, and accelerating transcytosis across the blood-brain barrier via megalin receptor and/or modulating activity of said receptor, for example activating or inhibiting signal transduction associated with this receptor, or activating or inhibiting biological function of the receptor;

capability of binding to a metallothionein and enhancing its neuroprotective and neuroregenerative functions.

According to the invention, biological activities of the peptide which are associated with physiological processes occurring in the brain or associated with normal or pathological conditions of the neural system are preferred. The molecular processes involving a biological activity of the peptide are preferably those that may be related to a cell of the neural system, more preferably to a neuronal cell. Accordingly, one of the preferred activities of the peptide according to the invention is the capability of stimulating neuronal cell differentiation.

The term "neuronal differentiation" is understood herein both as differentiation of neural precursor cells, or neural stem cells, and further differentiation of neural cells, such as for example maturation of neuronal cells. An example of such differentiation may be neurite outgrowth from immature neurons, branching of neurites, and also neuron regeneration.

Thus, one preferred embodiment the invention concerns biological activity of a peptide sequence associated with stimulating of differentiation of neural precursor/stem cells or immature neurons and/or stimulating neurite outgrowth from mature neurons, for examples neurons which were traumatizes but survived and are committed to regenerate damaged processes.

In the present context "differentiation" is related to the processes of maturation of neurons and extension of neurites, which take place after the last cell division of said neurons. The compounds of the present invention may be capable of stopping neural cell division and initiating maturation said cells, such as initiating extension of neurites. Otherwise, "differentiation" is related to initiation of the process of genetic, biochemical, morphological and physiological transformation of neuronal progenitor cells, immature neural cells or embryonic stem cells leading to formation of cells having functional characteristics of normal neuronal cell as such characteristics are defined in the art. The invention defines "immature neural cell" as a cell that has at least one feature of neural cell accepted in the art as a feature characteristic for the neural cell.

Substances with the potential to promote neurite outgrowth as well as stimulate regeneration and/or differentiation of neuronal cells, such as certain endogenous trophic factors, are prime targets in the search for compounds that facilitate for example neuronal regeneration and other forms of neuronal plasticity. To evaluate the potential of the present compound, the ability to stimulate the neurite outgrowth related signalling, interfere with cell adhesion, stimulate neurite outgrowth, regeneration of nerves, may be investigated. Compounds of the present invention are shown to promote neurite outgrowth and are therefore considered to be good promoters of regeneration of neuronal connections, and thereby of functional recovery after damages as well as promoters of neuronal function in other conditions where such effect is required.

According to the present invention a compound comprising at least one of the above peptide sequences is capable of stimulating neurite outgrowth. The invention concerns the neurite outgrowth improvement/stimulation such as about 75% improvement/stimulation above the value of neurite outgrowth of control/non-stimulated cells, for example 50%, such as about 150%, for example 100%, such as about 250, for example 200%, such as about 350%, for example 300%, such as about 450%, for example 400%, such as about 500%.

Estimation of capability of a candidate compound to stimulate neurite outgrowth may be done by using any known method or assay for estimation of neurite outgrowth, such as for example as the described in Examples below.

According to the invention a compound has neuritogenic activity both as an insoluble immobile component of cell growth substrate and as a soluble component of cell growth media. In the present context "immobile" means that the compound is bound/attached to a substance which is insoluble in water or a water solution and thereby it becomes insoluble in such solution as well. For medical applications both insoluble and soluble compounds are considered by the application, however soluble compounds are preferred. Under "soluble compound" is understood a compound, which is soluble in water or a water solution.

Accordingly, the invention also concerns a method for stimulating neuronal cell differentiation comprising using a peptide sequence of the invention or a compound comprising said sequence.

One of most preferred embodiments of the invention concerns the activity of the peptide sequences in connection with learning and memory, in particular, the capability of a peptide sequence to stimulate synaptic plasticity, spine formation, synaptic efficacy. Thus, the invention also concerns a method for stimulating memory and/or learning comprising using a peptide sequence of the invention and/or compound comprising said sequence. The invention relates to both short-term memory and long-term memory.

In another preferred embodiment of the invention a peptide sequence of the invention capable of stimulating cell survival, in particular neuronal cell survival. The invention concerns the capability of stimulating cell survival both due trauma and degenerative disease. Accordingly, the invention relates to a method for stimulating cell survival, preferably neuronal cell survival by using a peptide sequence of the invention and/or compound comprising said sequence.

Substances with the potential to enhance neuronal cells to survive due to damage as well as inhibit degeneration and/or apoptosis of neuronal cells in trauma and disease, are prime targets in the search for candidate compounds for new medicine for treatment of neurodegenerative diseases such as for example Alzheimer's or Parkinson's diseases. To evaluate the potential of the present peptides, the ability to stimulate survival related signalling, interfere with apoptosis related cellular reactions, stimulate regeneration of nerves may be investigated. Compounds of the present invention are shown to promote neural cell survival and decrease the cell loss and therefore considered to be good candidates for promotion of regeneration of neural connections in brain and/or in peripheral neural system, and thereby of functional recovery after damages due trauma or disease as well as promoters of neuronal function in any other conditions where such effect is required.

In the present context "survival" is related to the processes associated with maintenance and/or recovery of cell function after the damage of the cell. The compounds of the present invention may be capable of stopping or attenuating the processes committing the cell to death, such as inhibiting apoptosis of neural cells initiated by cell damage due trauma or disease. Otherwise, "survival" is related to inhibition of the processes associated with the cell damage leading to cell death and initiation of the processes of genetic, biochemical, morphological and physiological transformation or reconstruction of cells, in particular neuronal cells, such as progenitor cells, immature neural cells or embryonic stem cells or mature neural cells having normal functional characteristics defined in the art. The invention defines "immature neural cell" as a cell that has at least one feature of neural cell accepted in the art as a feature characteristic for the neural cell.

According to the present invention a compound comprising at least one of the above peptide sequences is capable of stimulating neural cell survival. The invention concerns the neural cell survival stimulation such as about 75% stimulation above the value of survival of control/non-stimulated cells, for example 50%, such as about 150%, for example 100%, such as about 250, for example 200%, such as about 350%, for example 300%, such as about 450%, for example 400%, such as about 500%.

Estimation of capability of a candidate compound to stimulate neural cell survival may be done by using any known method or assay for estimation of cell survival, such as for example the ones described in Examples of the present application.

According to the invention a compound has survival promoting activity both as insoluble and soluble compound. In the present context "insoluble" means that the compound is bound/attached to a substance which is insoluble in water or a water solution and thereby the compound becomes insoluble in such solution as well. For medical applications both insoluble and soluble compounds are considered by the application, however soluble compounds are preferred. Under "soluble compound" is understood a compound, which is soluble in water or a water solution.

In another embodiment the peptide sequence of the invention is also capable of inhibiting an inflammatory process, in particular an inflammatory process in the brain.

Inflammation is a defense reaction caused by tissue damage due to a mechanical injury or bacterial, virus or other organism infection. The inflammatory response involves three major stages: first, dilation of capillaries to increase blood flow; second, microvascular structural changes and escape of plasma proteins from the bloodstream; and third, leukocyte transmigration through endothelium and accumulation at the site of injury and infection. The inflammatory response begins with a release of inflammatory mediators. Inflammatory mediators are soluble, diffusible molecules that act locally at the site of tissue damage and infection, and at more distant sites, influencing consequent events of the inflammatory response. Inflammatory mediators can be exogenous, e. g. bacterial products or toxins, or endogenous, which are produced within the immune system itself, as well as injured tissue cells, lymphocytes, mast cells and blood proteins.

Neuroinflammation plays a prominent role in the progression of Alzheimer's disease and may be responsible for degeneration in vulnerable regions such as the hippocampus. Neuroinflammation is associated with elevated levels of extracellular glutamate and potentially an enhanced stimulation of glutamate N-methyl-D-aspartate receptors.

Anti-inflammatory activity is another important biological activity of the peptide sequence of the invention. Thus, the invention relates to anti-inflammatory peptide, which is capable of serving as an inhibitor of the sustained inflammatory response, in particular in the brain.

The continuous presence of inflammatory mediators, such as for example TNF alpha in the body in response to sustained presence of bacterial products or even live bacteria locally during days or weeks following trauma and/or infection promotes the reactions to inflammation, such as, for example, heat, swelling, and pain. The sustained inflammatory response has been proven to be very harmful to the body. If the bacterial products or live bacteria become spread universally in the body from their local focus the inflammatory reaction becomes overwhelming and out of control and leads to sepsis which eventually progress further to severe sepsis and septic shock. Anti-inflammatory peptides may be used to block or suppress the overwhelming sustained inflammatory response represented by a massive and harmful cytokine cascade in the blood and vital organs such as lung, liver intestine, brain and kidneys.

In the present context by the term "anti-inflammatory compound" is meant a compound which is capable of at least one of the following activities i) decreasing or inhibiting the gene expression in the immune cells, preferably monocytes/macrophages in response to bacterial products, live bacteria or trauma to produce endogenous inflammatory mediators including receptors for inflammatory mediators and transcription factors involved in the signal transduction of the inflammatory mediators, said mediators being preferably selected from the group comprising cytokines, selected from the group TNFalpha IL-1, IL-6, G-CSF, GM-CSF, M-CSF. Chemokines selected from the group comprising IL-8, MCP-1, receptors selected from the group Tissue factor and IL-2Ralpha, ii) decrease or inhibit the production bradykinin by the phase contact system, iii) decrease or inhibit the attractant potential for monocytes, and/or iv) decrease or inhibit the life-time of monocytes, neutrophils and other immune cells serving as an inducer of apoptosis, v) decrease or inhibit vascular endothelial cells to express the adhesion molecules, said adhesion molecules being preferably selected from the group comprising PECAM, ICAM-1, E-selectins, VCAM-1 vi) decrease or inhibit activation of the contact phase system to produce bradykinin leading to increased vascular permeability, vii) stimulate the synthesis of an anti-inflammatory mediator selected from the group of IL-10 and IL-12, viii) inhibiting complement activation;

ix) decreasing the risk of neural cell degeneration in the presence of chronic neuroinflammation, e.g. neurons which express glutamate N-methyl-D-aspartate receptors.

Another biological activity of a peptide of the invention which is preferred among others is the capability of the peptide of to bind to a receptor.

In the present content the term "receptor" is defined as a functional proteinaceous structure that tightly bind specific molecules (e.g. small molecules, proteins, viruses). The invention relates to receptors of the plasma membrane (surface) of cells, receptors which are located inside the cell's plasma membrane, i.e. free-floating receptors, soluble proteininaceous molecules, i.e. carrier proteins, receptors located inside the cell and associated with different compartments of said cell, e.g. nucleus, mitochondria.

Both (membrane, internal) types of receptors are a functional part of information transmission (i.e., signaling) to the cell. A general overview is that once bound, both the receptor and its "bound entity" as a complex is internalized by the cell via a process called endocytosis, in which the cell membrane in the vicinity of the bound complex invaginates. This process forms a membrane "bubble" on the inside of the cell, which then pinches off to form an endocytic vesicle. The receptor then is released from its bound entity by cleavage in the cell's lysosomes. It is recycled (returned) to the surface of the cell (e.g., low-density lipoprotein receptors). In some cases the receptor, along with its bound molecule may be degraded by the powerful hydrolytic enzymes found in the cell's lysosomes (e.g., insulin receptors, epidermal growth factor receptors, and nerve growth factor receptors). Endocytosis (internalization of receptors and bound ligand such as a hormone) removes hormones from the circulation and makes the cell temporarily less responsive to them because of the decrease in the number of receptors on the surface of the cell. Hence the cell is able to respond (to new signal).

The invention relates in a preferred embodiment to megallin receptor. The peptide sequence of the invention possesses a capability to bind to megallin, and activate megallin associated signal transduction, or activate signal transduction which is not directly associated with megalin. The latter mode of "reception" occurs when, following binding, a transmembrane protein (e.g., megalin) activates the portion of the transmembrane (i.e., through the cell membrane) protein lying inside the cell. That "activation" causes an effector inside cell to produce a "signal" chemical inside the cell which causes the cell's nucleus (via gene expression) to react to the original external chemical signal (that bound itself to the receptor portion of the transmembrane protein).

A peptide sequence of the invention has a capability to bind to megalin. As megalin is a scavenger receptor and has a plethora of ligands, the peptide sequence of the invention may competitively inhibit binding of the ligands to megalin and thus modulate the activity of said receptor associated with said ligands.

Another type of receptor of the sequence of the invention is soluble MT protein. A peptide sequence with is derived from a homophylic binding site of MT has a capability to bind to this homophylic site and therefore affect homophylic binding of one or more molecules of MT. This may have a major influence on function of MT which is of importance for a huge number of the body physiological processes. Accordingly, the invention relates to capability of binding a peptide sequence of the invention to MT as a preferable biological activity of the sequence as well.

4. Production of Individual Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4c (Russell et al., 1983, Nature 304:652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteines. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

By SAPS peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality.

When synthesised, individual peptide sequences may then be formulated as multimers using well-known in the art techniques, for examples dimers of the sequences may be obtained by the LPA method described in WO 00/18791, denrimeric polymers by the MAP synthesis described in PCT/US90/02039.

5. Antibody

It is another objective of the present invention to provide an antibody, antigen binding fragment or recombinant protein thereof capable of recognizing and selectively binding to an epitope comprising the motif of the invention or a sequence selected from SEQ ID NOs:1-64, or a fragment of said sequence, preferably the epitope located within the sequence of MT protein, for example metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-1I (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) or metallothionein-4 (MT4)

By the term "epitope" is meant the specific group of atoms (on an antigen molecule) that is recognized by (that antigen's) antibodies (thereby causing an immune response). The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta ($\beta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-85, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction.

(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256:495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in $E.$ $coli$ of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard method in the art for producing polyclonal and monoclonal antibodies using natural or recombinant fragments of human MT protein, such as metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-1I (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) or metallothionein-4 (MT4), said fragment comprising a structural motif of the invention, for example comprising a sequence selected from SEQ ID NOs: 9-64, such as for example a sequences selected from SEQ ID NOs: 1-64, as an antigen. Such antibodies may be also generated using variants, homologues or fragments of peptide sequences of SEQ ID NOs:1-64 said variants, homologues and fragments are immunogenic peptide sequences which meet the following criteria:
(i) being a contiguous amino acid sequence of at least 6 amino acids;
(ii) comprising the motif of the invention.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to antibodies which are capable of modulating, such as enhancing or attenuating, biological function of metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-11 (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) or metallothionein-4 (MT4), and to antibodies which do not modulate the function of MT upon binding to the epitope of the invention. Preferred biological functions of metallothionein-1 A (MT1A), metallothionein-1B (MT1B), metallothionein-1E (MT1E), metallothionein-1F (MT1F), metallothionein-1G (MT1G), metallothionein-1H (MT1H), metallothionein-1I (MT1I), metallothionein-1 K (MT1K), metallothionein-1 L (MT1L), metallothionein-1R (MT1R), metallothionein-1X (MT1 X), metallothionein-2 (MT2), metallothionein-3 (MT3) or metallothionein-4 (MT4)2 in the present context may be a capability of stimulating cell differentiation or cell survival, promoting nerve regeneration, inhibiting oxidative stress responses, activating astrocytes and their production of survival promoting growth factors and proteins, inhibiting inflammation, promoting morphological and functional plasticity of neural cells, e.g. enhancing synaptic plasticity promoting the formation of new functional synapses by newborn neurons.

6. Kit

The present invention discloses compounds that are capable of binding to MT. In one embodiment the invention relates to peptide sequences comprising the amino acid motif described above or comprising or consisting of a fragment of MT as described above. In another embodiment the invention relates to anti-MT antibodies capable of binding to the epitope described above. Both peptide sequences and antibody may be used for detection of MT in sample collected from an individual, for example a sample of a body fluid or biopsy.

In one aspect there is provided a kit for diagnosis of or for predicting the risk of a subject for developing a disease associated with MT function. Non-limited examples of use such a kit may be estimation of an increased risk for progression of primary melanoma (MT overexpression in a variety of cancers is associated with resistance to anticancer drugs and radiotherapy, and with a poor prognosis such diseases (Weinlich et al., Br J Dermatol. 2003, 149(3):535-41)), estimation of severity of chronic hepatitis C virus infection (HCV) (MT expression could reflect the severity of chronic HCV infection and could be one of the factors associated with a favorable clinical outcome in the response to interferon therapy (Carrera et al., Am J Gastroenterol. 2003, 98(5):1142-9)).

Thus, the invention a further embodiment relates to a diagnostic method comprising using a kit comprising a peptide sequence of the invention, compound of the invention and/or antibody of the invention. The diagnostic method is to be used for diagnosis of a disease wherein MT pays a role in pathology. The kit according to the invention may be used for detection of MT in a sample collected from an individual.

The sample used in the diagnostic method of the invention is any biological sample, such as for example a sample of blood, urine, body or tumor tissue, or any other appropriate biological sample.

In another embodiment there is provided a kit for inhibiting polymerization of MT in solution (MT aggregation is a serious problem and results in overestimation of the protein in patient samples (Tang et al. J Anal Toxicol. 1999 May-June; 23(3):153-8), polymerization of metallothioneins is also one of the usually encountered puzzles during the research process of metallothioneins' structure and function (Hou et al. Protein Sci. 2000 9(12):2302-12)).

A kit according of the invention preferably comprises at least one peptide sequence capable of binding to MT and/or at least one antibody or an antigen-binding fragment thereof, wherein said peptide sequence and/or said antibody or antibody fragment is linked to a detectable label.

The detectable label may be any type of label selected according to the detection method to be used. An appropriate label may be selected from any commercially available labels and used for labelling of any part of the kit of the invention, i.e. a peptide sequence, compound or/and antibody, according to the manufacturer instructions.

7. Pharmaceutical Composition

The invention also relates to a pharmaceutical composition comprising one or more of the compounds defined above, wherein the compound is capable of stimulating neurite outgrowth and/or neural cell differentiation, survival of neural cells and/or stimulating learning and/or memory. Thus, the invention concerns a pharmaceutical composition capable of stimulating differentiation of neuronal cells and/or stimulating regeneration of neuronal cells, and/or stimulating neuronal plasticity in connection with learning and memory, and/or stimulating survival of neural cells.

In the present context the term "pharmaceutical composition" is used synonymously with the term "medicament".

In a composition the peptide sequences may be formulated as comprising isolated individual peptide fragments or multimers or dimers thereof as discussed above.

The pharmaceutical composition may have the described above effects on cells in vitro or in vivo, wherein the composition is administered to a subject.

The medicament of the invention comprises an effective amount of one or more of the compounds as defined above, or a composition as defined above in combination with the pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, stimulating regeneration, plasticity and survival of neural cells in vitro or in vivo, said treatment involving administering an effective amount of one or more compounds as defined above.

Another strategy for administration is to implant or inject cells capable of expressing and secreting the compound in question. Thereby the compound may be produced at the location where it is going to act.

8. Treatment

Brain disorders like traumatic injury, pellagra dementia/toxicity; epilepsy, brain ischemic/stroke; EAE/MS (multiple sclerosis); and infectious encephalopathies; Amyotrophic Lateral Sclerosis, Parkinson's disease; peripheral nerve injury, cerebral malaria, ageing/age dementia, neuromuscular damage and diabetes, all, were associated with activity of MT. The MT roles were partially or fully validated in human tissue or human patients during degenerative diseases such as AD, Pick's disease and ALS; and during MS, Binswanger's encephalopathy, and ischaemia and during neuromuscular damage and diabetes. Also, during a number of common autoimmune, inflammatory and allergic diseases.

Thus, in a further aspect, the present invention relates to the above described peptides, fragments, or variants thereof, compounds and antibodies as medicaments for treatment of diseases wherein their
capability of stem cell differentiation, for example by stimulating neuronal cell precursor differentiation,
    capability of stimulating neural cell differentiation and/or regeneration of nerves, for example by stimulating neurite outgrowth,
    capability of stimulating neural plasticity associated with memory and learning, for example by stimulating synaptic efficacy,
    capability of stimulating of cell survival, in particular stimulating survival neuronal cells, for example by inhibiting apotosis of neural cells,
    capability of inhibiting the oxidative stress response, for example by stimulating expression of scavenges of reactive oxygen species,
    capability to activate astrogliosis, such as capability of stimulating astrocytes to express neuroprotective growth factors and proteins such as e.g. BDNF, NT-3, GDNF, neurturin, artemin, NGF, variety of fibroblast growth factors (FGFs), S100-proteins (S100A4, S100A6, S100A10, S100A12, S100B), IGF-2, neuregulin,
    capability of inhibiting inflammation, for example inhibiting the activation of microglia and macrophages, inhibiting expression of pro-inflammatory cytokines and/or by stimulating anti-inflammatory responses,
    capability of stimulating angiogenesis in the lesioned area, for example by stimulating expression of growth factor promoting angiogenesis such as VEGF and FGF2,
    capability of binding to a receptor, for example megalin receptor (Swiss-prot Ass. number: P98164) or MT protein, and accelerating transcytosis across the blood-brain barrier via megalin receptor and/or modulating activity of said receptor, for example activating or inhibiting signal transduction associated with this receptor, or activating or inhibiting biological function of the receptor,
    capability of binding to a metallothionein and enhancing its neuroprotective and neuroregenerative functions
may be essential for curing.

Treatment by the use of the compounds/compositions according to the invention is in one embodiment useful for inducing differentiation, modulating proliferation, stimulate regeneration, neuronal plasticity and survival of cells being resident or implanted or transplanted.

Thus, the treatment comprises treatment and/or prophylaxis of cell damage and/or cell death in relation to diseases or conditions of the central and peripheral nervous system, such as postoperative nerve damage, traumatic neuron damage, e.g. resulting from spinal cord injury, impaired myelination of nerve fibers, postischemic damage, e.g. resulting from a stroke, multiinfarct dementia, multiple sclerosis, neuronal degeneration associated with diabetes mellitus, neuro-muscular degeneration, schizophrenia, Alzheimer's disease, Parkinson's disease, or Huntington's disease Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

In yet a further embodiment the use of the compound and/or pharmaceutical composition is for the stimulation of the ability to learn and/or of the short and/or long term memory.

In particular the compound and/or pharmaceutical composition of the invention may be used in the treatment of clinical conditions, such as psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nerve system and sense organs, cognitive anomalies, inflammatory disease of the central nervous system, such as meningitis, encephalitis, Cerebral degenerations such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis; peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis, neoplasms such as malignant neoplasms, benign neoplasms, carcinoma in situ and neoplasms of uncertain behavior, more specifically cancer in breast, thyroidal, pancreas, brain, lung, kidney, prostate, liver, heart, skin, blood organ (incl. but not limited to CML and AML), muscles (sarcoma), cancers with dysfunction and/or over- or under-expression of specific receptors and/or expression of mutated receptors or associated with soluble receptors, such as but not limited to Erb-receptors and FGF-receptors; autoimmune disorders, such as rheumatoid arthritis, SLE, ALS and MS, anti-inflammatory effects, amyloidosis, chronic rheumatic heart disease, ischaemic heart disease, arrhythmia, asthma and other allergic reactions; diseases in the pulmonary system, respiratory system, sensoring e.g. oxygene. astma, complications of the administration of anesthetic or other sedation in labor and delivery, acute myocardial infarction, and other related disorders or sequel from AMI; metabolic disorders, such as obscenity lipid disorders (e.g. hyper cholestorolamia, artheslerosis), diabetes type I and II, diseases of endocrine glands, such as diabetes mellitus I and II, pituitary gland tumor, disorders of amino-acid transport and metabolism, disorders of purine and pyrimidine metabolism and gout, myelopathy, drug-induced, radiation-induced, myelitis, bone disorders, such as fracture, osteoporosis, osteo arthritis (OA), obesity; stem cell protection or maturation in vivo or in vitro, neurogenesis.

Inflammation of the brain is often consequence of infection, autoimmune processes, toxins, and other conditions. Viral infections are a relatively frequent cause of this condition. Encephalitis may occur as primary or secondary manifestation of TOGAVIRIDAE INFECTIONS; HERPESVIRIDAE INFECTIONS; ADENOVIRIDAE INFECTIONS; FLAVIVIRIDAE INFECTIONS; BUNYAVIRIDAE INFECTIONS; PICORNAVIRIDAE INFECTIONS; PARAMYXOVIRIDAE INFECTIONS; ORTHOMYXOVIRIDAE INFECTIONS; RETROVIRIDAE INFECTIONS; and ARENAVIRIDAE INFECTIONS.

Accordingly, a peptide, compound or a pharmaceutical composition of the invention may be used for treatment inflammation in the brain associated with a viral infection.

A large body of clinical and experimental data indicate that complement activation is an important mechanism for neuronal and glial injury in Guillain-Barré syndromes. Inhibition of complement activation therefore might be expected to limit the progression of the disease (Halstead et al. (2005) Annals of Neurology 58:203-21).

Thus, in another embodiment, a peptide sequence, a compound and pharmaceutical composition may be used for treatment of Guillain-Barré syndrome, its variant forms, such as Miller Fisher syndrome, and other complement dependent neuro-muscular disorders.

Peptide sequences, compounds and pharmaceutical composition may also be used for treatment children with autism.

Autism is a brain disorder that begins in early childhood and persists throughout adulthood; affects three crucial areas of development: communication, social interaction, and creative or imaginative play. It is estimated to afflict between 2 and 5 of every 1000 children and is four times more likely to strike boys than girls. Children with autism have difficulties in social interaction and communication and may show repetitive behaviour and have unusual attachments to objects or routines.

In recent years, there have been scientific hints of immune system irregularities in children with autism.

Thus, a peptide sequence, compound or a composition comprising thereof may advantageously be used for treatment inflammation, in particular inflammation of the brain.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide. Thus, in a further aspect, the present invention relates to a prosthetic nerve guide, characterised in that it comprises one or more of the compounds or the pharmaceutical composition as defined above. Nerve guides are known in the art.

Another aspect of the invention relates to the use of a compound as defined above. In particular the use of a compound according to the invention is for the production of a pharmaceutical composition. The pharmaceutical composition is preferably for the treatment or prophylaxis of any of the diseases and conditions mentioned above.

In yet a further aspect the invention relates to a method of treating a disease or condition as discussed above by administering a compound as defined herein.

Examples

Peptides

MTAn:
KKSSCSCSPVGSAK
(SEQ ID NO: 1)

MTAc:
AQGSISKGASDKSS
(SEQ ID NO: 2)

MTBn:
MDPNSSSAAGDSST
(SEQ ID NO: 3)

MTBc:
SAGSSKSKESKSTS
(SEQ ID NO: 4)

MTAcc:
AQGSICKGASDKSS
(SEQ ID NO: 5)

MTBnc:
MDPNCSCAAGDSST
(SEQ ID NO: 6)

MTBcc:
SAGSCKCKESKSTS
(SEQ ID NO: 7)

MT3Ip:
KGGEAEAEAEK
(SEQ ID NO: 8)

Neuronal Differentiation
Methods

Primary cultures of cerebellar granule neurons (CGN) from seven days old rats were plated at a density of 10,000 cells/cm$^2$ in eight-well permanox chamber slides and left to differentiate for 24 hours in the presence of various concentrations of peptide. Cells were fixated and immuno-stained for GAP-43 to visualise only neurons. CGN cultures were fixed in 4% paraformaldehyde followed by blocking with 1% BSA and then incubated with polyclonal rabbit antibodies against rat GAP-43 (Chemicon, AH Diagnostics, Aarhus, Denmark) (1:1000 dilution with 1% BSA) followed by incubation with secondary Alexa Fluor®488 goat anti-rabbit antibodies (Molecular Probes, Eugene, Oreg., USA) (1:700 dilution with 1% BSA. Neurite length was estimated by means of a stereological approach (Rønn et al., 2000). Results are expressed as percentage neurite outgrowth±SEM, with the untreated controls set at 100%. Statistics are performed with a Student's paired t-test. *=p<0.05, =p<0.01, *=p<0.001. If not specifically indicated, four experiments were performed for each condition.

2. Results

Dissociated neurons from the cerebellum (CGN) were grown for 24 h in the presence of the individual peptides. From FIGS. 1-5, it appears that the peptides MTAc, MTBc, MTAcc, MTBnc and MTBcc stimulated differentiation of cerebellar primary neurons. The induction of neurite extension by all peptides was dose-dependent with a bell-shaped curve. The effect of the peptides MTBn and MTP31p was also tested, and it was found that these peptides had no neuritogenic activity.

Neuronal Survival In Vitro
Methods
1. Cell Survival Assay

Primary CGN cultures from seven days old rats were plated at a density of 100,000 cells/cm$^2$ in eight-well permanox chamber slides coated with poly-D-Lysine and grown in a medium supplemented with 40 mM KCl. After 24 hours cytosine-β-D-arabinofuranoside was added to the culture to inhibit proliferation of non-neuronal cells. Neurons were left to differentiate for further 6 days in vitro, before apoptosis was induced by shifting cells into a starving medium containing either 5 mM KCl alone (negative control), 40 mM KCl (positive control) or 5 mM KCl plus various concentrations of peptide. 48 hours after apoptosis induction cells were fixated and stained with Hoechst 33258. Neuronal viability was estimated by comparing the amount of live neurons with the total number of neurons based on nuclear morphology. Results (see FIGS. 6-9) from at least four independent experiments are expressed as percentage survival±SEM, with the negative control set at 100%. Statistics are performed with a Student's paired t-test. *=p<0.05, =p<0.01, *=p<0.001.

2. TUNEL Assay (DNA Fragmentation)

Figure 10:
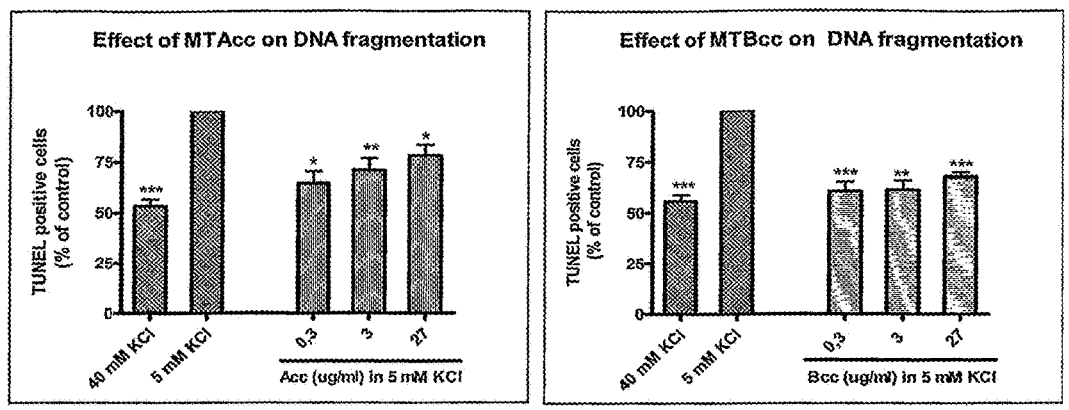
FIG. 10 Effect of the MTAcc and MTBcc peptides on DNA fragmentation.

Primary cultures of seven days old rats were plated, cultured and induced to undergo apoptosis as described above for neuronal survival, however cells were fixated 24 hour after apoptosis induction. By using the Fluorescien FragEL DNA fragmentation Kit, which label free DNA ends with a green fluorescent colour, the amount of neurons undergoing DNA fragmentation can be estimated and compared to the total amount of cells, which are stained with propidium iodide. Results (see FIG. 10) from at least four independent experiments are expressed as percentage TUNEL positive cells±SEM, with the negative control set at 100%. Statistics are performed with a Student's paired t-test. *=p<0.05, =p<0.01, *=p<0.001.

Results

CGN from 7-day-old rats were induced to differentiate for 7 days in a medium with a high potassium concentration after which the neurons were grown for two days in a low potassium medium either in the absence or presence of IGF-1 (positive control), or the MT-derived peptides. As appears from FIGS. 6-9, cell death induced by reducing the potassium concentration in the medium could be prevented by treatment with IGF-1. Moreover, treatment with the MT-derived peptides, MTAc, MTBc, MTBn, MTAcc, MTBcc, MTBnc and MT31p, all promoted survival of CGN in a dose dependent manner.

The anti-apoptotic effect of the MT-derived peptides was confirmed using a DNA fragmentation assay. From FIG. 10 it appears that treatment with the peptides MTAcc and MTBcc strongly reduced the number of apoptotic neurons.

Neuronal Rescue and Tissue Repair In Vivo
Methods

A focal brain injury on the right fronto-parietal cortex was made by applying a piece of dry-ice (−78° C.) directly onto the skull for 30 seconds in mice and 60 seconds in rats, as previously described in detail (Penkowa and Moos, 1995). The rats were treated s.c. with the tetrameric form of the MTAcc peptide (AQGSICKGASDKSS) (SEQ ID NO:5) one day before lesion and one and two days after the lesion (10 mg/kg bodyweight/injection). Three days after the lesion animals were fixed by transcardial perfusion with paraformaldehyde. Histochemistry and immunohistochemistry (IHC) were performed on sections cut from organs taken from fixated animals. For immunohistochemical investigation, brains were dissected and postfixed in Zamboni's fixative for 2-3 hours, dehydraded in graded alcohol followed by xylol and subsequently embedded in paraffin before being cut in 3 μm frontal sections throughout the entire area of the lesion. Terminal deoxynucleotidyl transferase (TdT)-mediated deoxyuridine triphosphate (dUTP)-biotin nick end labeling (TUNEL) was performed using the Fragment End Labeling (FragEL™) Detection Kit (Calbiochem, USA, code QIA33). The FragEL kit contains all the materials used below and each step was performed according to the manufacturer's recommendations. Sections were also immunostained for markers of oxidative stress such as peroxynitrite-induced nitration of tyrosine residues (NITT) and malondialdehyde (MDA) and for markers of inflammation such as interleukin (IL)-1, IL-12 and tumor necrosis factor (TNF) a, as described by Penkowa et al. (2000).

Results

Figure 11:
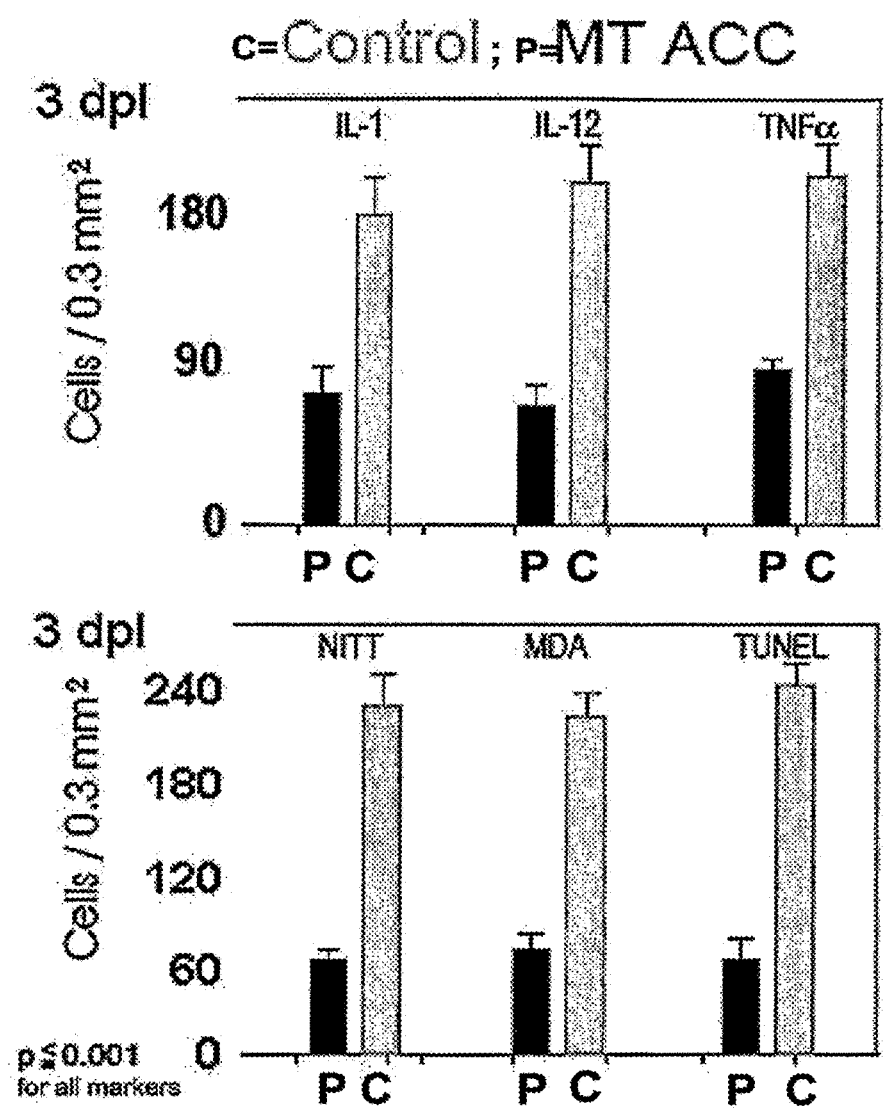
FIG. 11 Effect of the MTAcc peptide on neuronal survival in vivo demonstrated as the counts of cells demonstrating immunostaining for selected markers of inflammation (IL-1, IL12 and THFα), oxidative stress (NITT and MDA) and apoptotic cell death (TUNEL)
FIG. 12 Binding of the MTAcc peptide to MT studied by means of SPR analysis. Approximately 2000 resonance units (RU) of the MT2 protein (Sigma) were immobilized on the sensor chip. The binding is given as the response difference between the binding to the sensor chip with the immobilized MT2 and a blank sensor chip (unspecific binding). The peptide was injected into the sensor chip at a concentration of 0.87 µM. The experiment was repeated four times.
Figure 12:
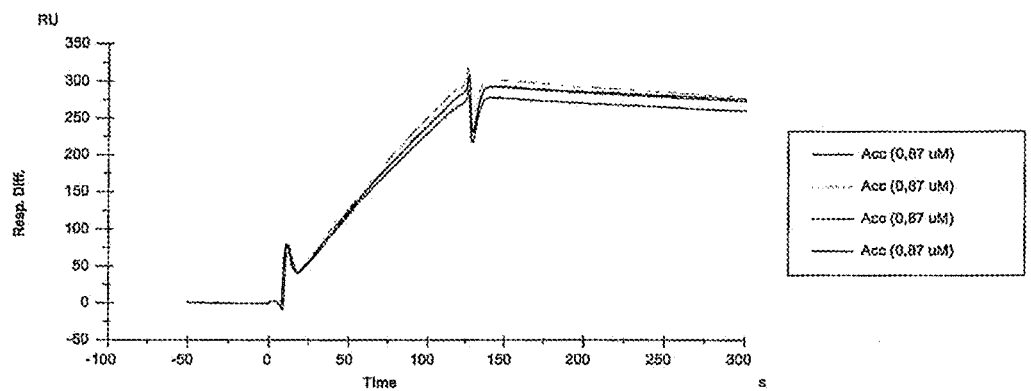
Figure 13:
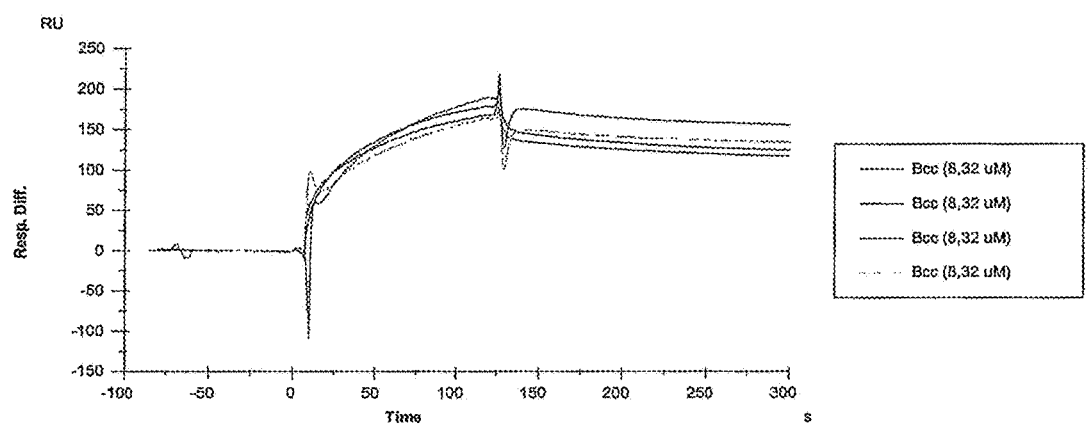
FIG. 13 Binding of the MTBcc peptide to MT studied by means of SPR analysis. Approximately 2000 resonance units (RU) of the MT2 protein (Sigma) were immobilized on the sensor chip. The binding is given as the response difference between the binding to the sensor chip with the immobilized MT2 and a blank sensor chip (unspecific binding). The peptide was injected into the sensor chip at a concentration of 8.32 µM. The experiment was repeated four times.
Figure 14:
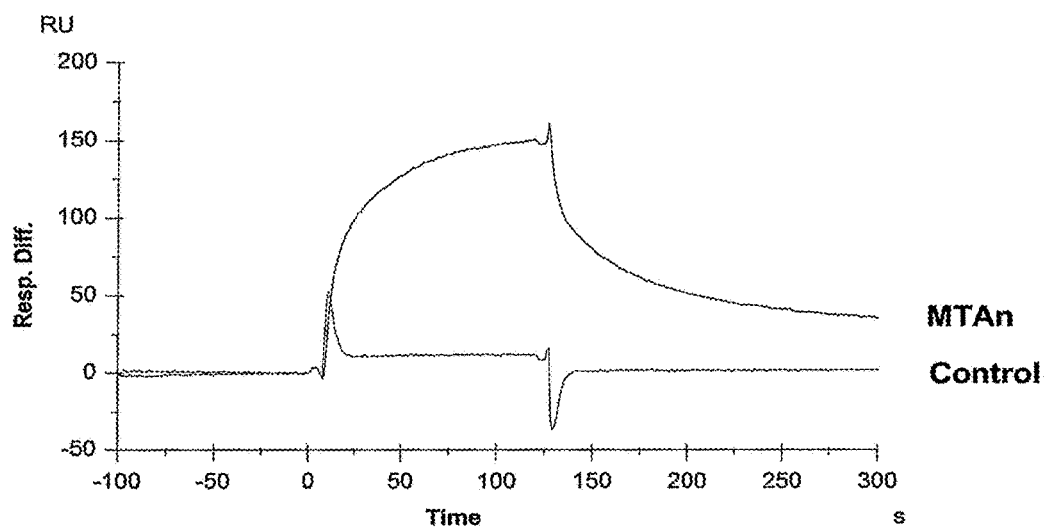
FIG. 14 Binding of the MTAn peptide to MT studied by means of SPR analysis. Approximately 2000 resonance units (RU) of the MT2 protein (Sigma) were immobilized on the sensor chip. The binding is given as the response difference between the binding to the sensor chip with the immobilized MT2 and a blank sensor chip (unspecific binding). The peptide was injected into the sensor chip at a concentration of 1.7 µM.

From FIG. 11 it can be seen that treatment of rats with the MTAcc peptide resulted in a dramatic decrease of the number of apoptotic cell (determined by TUNEL staining), inhibition of oxidative stress (determined by NITT and MDA immunostaining) and inhibition of the inflammatory response to the lesion (determined by immunostaining for inflammatory markers IL-1, IL-12 and TNFα).

Binding Peptides to MT2 Protein In Vitro
Methods
Surface Plasmon Resonance (SPR) Analysis Analysis of binding was performed employing a BIAcoreX instrument (Biosensor AB, Uppsala, Sweden) at 25° C. using 10 mM pH 7.4 sodium phosphate containing 150 mM NaCl as running buffer (phosphate-buffered saline, PBS). The flow-rate was 5 μl/min. Data were analysed by non-linear curve-fitting using the manufacturer's software. The MT2 protein (from Sigma) was immobilized on a sensor chip CM5 using an amine coupling kit (Biosensor AB) as follows: the chip was activated by 20 µl activation solution; the protein was immobilized using 12 µl 20 µg/ml protein in 10 mM sodium phosphate buffer pH 6.0; the chip was blocked by 35 µl blocking solution. Various peptides at the indicated concentrations were injected into the sensor chip. The curve corresponding to the difference between binding to MT2 and a blank chip was used for analysis.

Results

It is known that MT can oligomerize in biological fluids (Tang et al., 1999), although the mechanism and the binding sites responsible for polymerization are not known. By employing SPR we tested whether peptides derived from MT can bind to the MT protein. From FIGS. 1, 2 and 3 it appears that the peptides MTAcc, MTBcc and MTAn specifically bind to the immobilized on a sensor chip MT2 protein with the equilibrium dissociated constants (Kd) indicated in Table 1.

TABLE 1

| | Affinity binding constants | | |
|---|---|---|---|
| | $k_a$ (M$^{-1}$ s$^{-1}$) | $k_d$ (s$^{-1}$) | $K_D$ (M) |
| MT-2:MTAcc | 4.54 ± 0.21 × 10$^3$ | 4.00 ± 0.27 × 10$^{-4}$ | 8.95 ± 1.00 × 10$^{-8}$ |
| MT-2:MTBcc | 2.83 ± 0.93 × 10$^3$ | 5.01 ± 1.75 × 10$^{-4}$ | 1.60 ± 0.23 × 10$^{-7}$ |
| MT-2:MTAn | 1.57 ± 0.05 × 10$^4$ | 5.74 ± 0.19 × 10$^{-3}$ | 3.67 ± 0.16 × 10$^{-7}$ |

The invention claimed is:

1. A method for stimulating neurite outgrowth, neural cell survival, neural cell differentiation, neural plasticity associated with learning and memory, and/or inhibiting inflammation, comprising a step of administering a peptide consisting of not more than 20 amino acids in length, wherein the peptide comprises the amino acid sequence SAGSCKCKESKSTS (SEQ ID NO:7) or a variant of SEQ ID NO:7, said variant having at least 90% sequence identity to SEQ ID NO:7.

2. A method for stimulating neurite outgrowth, neural cell survival, neural cell differentiation, neural plasticity associated with learning and memory, and/or inhibiting inflammation, comprising a step of administering the peptide of claim 1, comprising an amino acid motif of the formula: S/D/E-(x)$_n$-S/D/E-K/S, wherein (x)$_n$ is a sequence of any amino acid residues, and n is an integer from 4 to 5.

3. A method for stimulating neurite outgrowth, neural cell survival, neural cell differentiation, neural plasticity associated with learning and memory, and/or inhibiting inflammation, comprising a step of administering the peptide according to claim 2, wherein n is 4.

4. A method for stimulating neurite outgrowth, neural cell survival, neural cell differentiation, neural plasticity associated with learning and memory, and/or inhibiting inflammation, comprising a step of administering the peptide according to claim 2, wherein n is 5.

5. A method for stimulating neurite outgrowth, neural cell survival, neural cell differentiation, neural plasticity associated with learning and memory, and/or inhibiting inflammation, comprising a step of administering the peptide according to claim 2, wherein the amino acid sequence (x) comprises at least one of K, S, E, and C.

6. A method for stimulating neurite outgrowth, neural cell survival, neural cell differentiation, neural plasticity associated with learning and memory, and/or inhibiting inflammation, comprising a step of administering the peptide according to claim 2, wherein said peptide comprises at least one amino acid residue G within a sequence of 10 amino acid residues comprising the motif.

7. A method for stimulating neurite outgrowth, neural cell survival, neural cell differentiation, neural plasticity associated with learning and memory, and/or inhibiting inflammation, comprising a step of administering the peptide according to claim 6, wherein said amino acid residue G immediately precedes an amino acid residue S/D/E of said motif.

8. A method for stimulating neurite outgrowth, neural cell survival, neural cell differentiation, neural plasticity associated with learning and memory, and/or inhibiting inflammation, comprising a step of administering a peptide according to claim 1, wherein said peptide consists of the amino acid sequence of SEQ ID NO:7.

9. A method for stimulating neurite outgrowth, neural cell survival, neural cell differentiation, neural plasticity associated with learning and memory, and/or inhibiting inflammation, comprising a step of administering a compound comprising one or more peptides, wherein each of said one or more peptides consists of not more than 20 amino acids in length, wherein each of said one or more peptides comprises the amino acid sequence SAGSCKCKESKSTS (SEQ ID NO:7) or a variant of SEQ ID NO:7, said variant having at least 90% sequence identity to SEQ ID NO:7.

10. The method according to claim 9, wherein said compound comprising one or more peptides consists of a single peptide.

11. The method according to claim 9, wherein said compound comprising one or more peptides comprises two or more of said peptide.

12. The compound according to claim 11 comprising a dimer or a tetramer of said peptide.

13. The compound according to claim 11 comprising a dendrimer of said peptide.

14. A method for stimulating neurite outgrowth, neural cell survival, neural cell differentiation, neural plasticity associated with learning and memory, and/or inhibiting inflammation, comprising a step of administering a pharmaceutical composition comprising a peptide consisting of not more than 17 amino acids in length, wherein the peptide comprises the amino acid sequence SAGSCKCKESKSTS (SEQ ID NO:7) or a variant of SEQ ID NO:7, said variant having at least 90% sequence identity to SEQ ID NO:7.

15. A method for stimulating neurite outgrowth, neural cell survival, neural cell differentiation, neural plasticity associated with learning and memory, and/or inhibiting inflammation, comprising a step of administering a pharmaceutical composition comprising a peptide consisting of not more than 20 amino acids in length, wherein the peptide comprises the amino acid sequence SAGSCKCKESKSTS (SEQ ID NO:7) or a variant of SEQ ID NO:7, said variant having at least 90% sequence identity to SEQ ID NO:7.

* * * * *

SEQUENCE LISTING

<160> NUMBER OF SEQ ID NOS: 64

<210> SEQ ID NO 1
<211> LENGTH: 14
<212> TYPE: PRT
<213> ORGANISM: Homo sapiens

<400> SEQUENCE: 1

Lys Lys Ser Ser Cys Ser Cys Ser Pro Val Gly Ser Ala Lys
1               5                   10

<210> SEQ ID NO 2
<211> LENGTH: 14
<212> TYPE: PRT
<213> ORGANISM: Homo sapiens

<400> SEQUENCE: 2

Ala Gln Gly Ser Ile Ser Lys Gly Ala Ser Asp Lys Ser Ser
1               5                   10

<210> SEQ ID NO 3
<211> LENGTH: 14
<212> TYPE: PRT
<213> ORGANISM: Homo sapiens

<400> SEQUENCE: 3

Met Asp Pro Asn Ser Ser Ser Ala Ala Gly Asp Ser Ser Thr
1               5                   10

<210> SEQ ID NO 4
<211> LENGTH: 14
<212> TYPE: PRT
<213> ORGANISM: Homo sapiens

<400> SEQUENCE: 4

Ser Ala Gly Ser Ser Lys Ser Lys Glu Ser Lys Ser Thr Ser
1               5                   10

<210> SEQ ID NO 5
<211> LENGTH: 14
<212> TYPE: PRT
<213> ORGANISM: Homo sapiens

<400> SEQUENCE: 5

Ala Gln Gly Ser Ile Cys Lys Gly Ala Ser Asp Lys Ser Ser
1               5                   10

```
<210> SEQ ID NO 6
<211> LENGTH: 14
<212> TYPE: PRT
<213> ORGANISM: Homo sapiens

<400> SEQUENCE: 6

Met Asp Pro Asn Cys Ser Cys Ala Ala Gly Asp Ser Ser Thr
1               5                   10

<210> SEQ ID NO 7
<211> LENGTH: 14
<212> TYPE: PRT
<213> ORGANISM: Homo sapiens

<400> SEQUENCE: 7

Ser Ala Gly Ser Cys Lys Cys Lys Glu Ser Lys Ser Thr Ser
1               5                   10

<210> SEQ ID NO 8
<211> LENGTH: 12
<212> TYPE: PRT
<213> ORGANISM: Homo sapiens

<400> SEQUENCE: 8

Lys Gly Gly Glu Ala Ala Glu Ala Glu Ala Glu Lys
1               5                   10

<210> SEQ ID NO 9
<211> LENGTH: 14
<212> TYPE: PRT
<213> ORGANISM: Homo sapiens

<400> SEQUENCE: 9

Lys Lys Ser Cys Cys Ser Cys Cys Pro Met Ser Cys Ala Lys
1               5                   10

<210> SEQ ID NO 10
<211> LENGTH: 14
<212> TYPE: PRT
<213> ORGANISM: Homo sapiens

<400> SEQUENCE: 10

Lys Lys Cys Cys Cys Ser Cys Cys Pro Val Gly Cys Ala Lys
1               5                   10

<210> SEQ ID NO 11
<211> LENGTH: 14
<212> TYPE: PRT
<213> ORGANISM: Homo sapiens

<400> SEQUENCE: 11

Lys Lys Ser Cys Cys Ser Cys Cys Pro Val Gly Cys Ala Lys
1               5                   10

<210> SEQ ID NO 12
<211> LENGTH: 14
<212> TYPE: PRT
<213> ORGANISM: Homo sapiens

<400> SEQUENCE: 12

Lys Lys Ser Cys Cys Ser Cys Cys Pro Val Gly Cys Ser Lys
1               5                   10
```

```
<210> SEQ ID NO 13
<211> LENGTH: 14
<212> TYPE: PRT
<213> ORGANISM: Homo sapiens

<400> SEQUENCE: 13

Lys Lys Ser Cys Cys Ser Cys Cys Pro Val Gly Cys Ala Lys
1               5                   10

<210> SEQ ID NO 14
<211> LENGTH: 14
<212> TYPE: PRT
<213> ORGANISM: Homo sapiens

<400> SEQUENCE: 14

Lys Lys Ser Cys Cys Ser Cys Cys Pro Leu Gly Cys Ala Lys
1               5                   10

<210> SEQ ID NO 15
<211> LENGTH: 14
<212> TYPE: PRT
<213> ORGANISM: Homo sapiens

<400> SEQUENCE: 15

Lys Lys Ser Cys Cys Ser Cys Cys Pro Val Gly Cys Ala Lys
1               5                   10

<210> SEQ ID NO 16
<211> LENGTH: 14
<212> TYPE: PRT
<213> ORGANISM: Homo sapiens

<400> SEQUENCE: 16

Lys Lys Ser Cys Cys Ser Cys Cys Pro Val Gly Cys Ala Lys
1               5                   10

<210> SEQ ID NO 17
<211> LENGTH: 14
<212> TYPE: PRT
<213> ORGANISM: Homo sapiens

<400> SEQUENCE: 17

Lys Lys Ser Cys Cys Ser Cys Cys Pro Val Gly Cys Ala Lys
1               5                   10

<210> SEQ ID NO 18
<211> LENGTH: 14
<212> TYPE: PRT
<213> ORGANISM: Homo sapiens

<400> SEQUENCE: 18

Lys Lys Ser Cys Cys Ser Cys Cys Pro Met Gly Cys Ala Lys
1               5                   10

<210> SEQ ID NO 19
<211> LENGTH: 14
<212> TYPE: PRT
<213> ORGANISM: Homo sapiens

<400> SEQUENCE: 19

Lys Lys Ser Cys Cys Ser Cys Cys Pro Val Gly Cys Ala Lys
1               5                   10
```

```
<210> SEQ ID NO 20
<211> LENGTH: 14
<212> TYPE: PRT
<213> ORGANISM: Homo sapiens

<400> SEQUENCE: 20

Lys Lys Ser Cys Cys Ser Cys Cys Pro Val Gly Cys Ala Lys
1               5                   10

<210> SEQ ID NO 21
<211> LENGTH: 14
<212> TYPE: PRT
<213> ORGANISM: Homo sapiens

<400> SEQUENCE: 21

Lys Lys Ser Cys Cys Ser Cys Cys Pro Ala Glu Cys Glu Lys
1               5                   10

<210> SEQ ID NO 22
<211> LENGTH: 14
<212> TYPE: PRT
<213> ORGANISM: Homo sapiens

<400> SEQUENCE: 22

Arg Lys Ser Cys Cys Pro Cys Cys Pro Gly Cys Ala Lys
1               5                   10

<210> SEQ ID NO 23
<211> LENGTH: 14
<212> TYPE: PRT
<213> ORGANISM: Homo sapiens

<400> SEQUENCE: 23

Ala Gln Gly Cys Ile Cys Lys Gly Ala Ser Glu Lys Cys Ser
1               5                   10

<210> SEQ ID NO 24
<211> LENGTH: 14
<212> TYPE: PRT
<213> ORGANISM: Homo sapiens

<400> SEQUENCE: 24

Ala Gln Gly Cys Val Cys Lys Gly Ser Ser Glu Lys Cys Ser
1               5                   10

<210> SEQ ID NO 25
<211> LENGTH: 14
<212> TYPE: PRT
<213> ORGANISM: Homo sapiens

<400> SEQUENCE: 25

Ala Gln Gly Cys Val Cys Lys Gly Ala Ser Glu Lys Cys Ser
1               5                   10

<210> SEQ ID NO 26
<211> LENGTH: 14
<212> TYPE: PRT
<213> ORGANISM: Homo sapiens

<400> SEQUENCE: 26

Ala Gln Gly Cys Val Cys Lys Gly Ala Ser Glu Lys Cys Ser
1               5                   10
```

```
<210> SEQ ID NO 27
<211> LENGTH: 14
<212> TYPE: PRT
<213> ORGANISM: Homo sapiens

<400> SEQUENCE: 27

Ala Gln Gly Cys Ile Cys Lys Gly Ala Ser Glu Lys Cys Ser
1               5                   10

<210> SEQ ID NO 28
<211> LENGTH: 14
<212> TYPE: PRT
<213> ORGANISM: Homo sapiens

<400> SEQUENCE: 28

Ala Gln Gly Cys Ile Cys Lys Gly Ala Ser Glu Lys Cys Ser
1               5                   10

<210> SEQ ID NO 29
<211> LENGTH: 14
<212> TYPE: PRT
<213> ORGANISM: Homo sapiens

<400> SEQUENCE: 29

Ala Gln Gly Cys Ile Cys Lys Gly Ala Ser Glu Lys Cys Ser
1               5                   10

<210> SEQ ID NO 30
<211> LENGTH: 14
<212> TYPE: PRT
<213> ORGANISM: Homo sapiens

<400> SEQUENCE: 30

Ala Gln Gly Cys Ile Cys Lys Gly Ala Ser Glu Lys Cys Ser
1               5                   10

<210> SEQ ID NO 31
<211> LENGTH: 14
<212> TYPE: PRT
<213> ORGANISM: Homo sapiens

<400> SEQUENCE: 31

Ala Gln Gly Cys Ile Cys Lys Gly Thr Ser Asp Lys Cys Ser
1               5                   10

<210> SEQ ID NO 32
<211> LENGTH: 14
<212> TYPE: PRT
<213> ORGANISM: Homo sapiens

<400> SEQUENCE: 32

Ala Gln Gly Cys Val Cys Lys Gly Ala Ser Glu Lys Cys Ser
1               5                   10

<210> SEQ ID NO 33
<211> LENGTH: 14
<212> TYPE: PRT
<213> ORGANISM: Homo sapiens

<400> SEQUENCE: 33

Ala Gln Gly Cys Ile Cys Lys Gly Thr Ser Asp Lys Cys Ser
1               5                   10
```

```
<210> SEQ ID NO 34
<211> LENGTH: 14
<212> TYPE: PRT
<213> ORGANISM: Homo sapiens

<400> SEQUENCE: 34

Ala Gln Gly Cys Ile Cys Lys Gly Ala Ser Asp Lys Cys Ser
1               5                   10

<210> SEQ ID NO 35
<211> LENGTH: 20
<212> TYPE: PRT
<213> ORGANISM: Homo sapiens

<400> SEQUENCE: 35

Ala Lys Asp Cys Val Cys Lys Gly Gly Glu Ala Ala Glu Ala Glu Ala
1               5                   10                  15

Glu Lys Cys Ser
            20

<210> SEQ ID NO 36
<211> LENGTH: 14
<212> TYPE: PRT
<213> ORGANISM: Homo sapiens

<400> SEQUENCE: 36

Ala Arg Gly Cys Ile Cys Lys Gly Gly Ser Asp Lys Cys Ser
1               5                   10

<210> SEQ ID NO 37
<211> LENGTH: 14
<212> TYPE: PRT
<213> ORGANISM: Homo sapiens

<400> SEQUENCE: 37

Met Asp Pro Asn Cys Ser Cys Ala Thr Gly Gly Ser Cys Thr
1               5                   10

<210> SEQ ID NO 38
<211> LENGTH: 14
<212> TYPE: PRT
<213> ORGANISM: Homo sapiens

<400> SEQUENCE: 38

Met Asp Pro Asn Cys Ser Cys Thr Thr Gly Gly Ser Cys Ala
1               5                   10

<210> SEQ ID NO 39
<211> LENGTH: 14
<212> TYPE: PRT
<213> ORGANISM: Homo sapiens

<400> SEQUENCE: 39

Met Asp Pro Asn Cys Ser Cys Ala Thr Gly Gly Ser Cys Thr
1               5                   10

<210> SEQ ID NO 40
<211> LENGTH: 14
<212> TYPE: PRT
<213> ORGANISM: Homo sapiens

<400> SEQUENCE: 40

Met Asp Pro Asn Cys Ser Cys Ala Ala Gly Val Ser Cys Thr
1               5                   10
```

```
<210> SEQ ID NO 41
<211> LENGTH: 14
<212> TYPE: PRT
<213> ORGANISM: Homo sapiens

<400> SEQUENCE: 41

Met Asp Pro Asn Cys Ser Cys Ala Ala Gly Val Ser Cys Thr
1               5                   10

<210> SEQ ID NO 42
<211> LENGTH: 14
<212> TYPE: PRT
<213> ORGANISM: Homo sapiens

<400> SEQUENCE: 42

Met Asp Pro Asn Cys Ser Cys Glu Ala Gly Gly Ser Cys Ala
1               5                   10

<210> SEQ ID NO 43
<211> LENGTH: 14
<212> TYPE: PRT
<213> ORGANISM: Homo sapiens

<400> SEQUENCE: 43

Met Asp Pro Asn Cys Ser Cys Ala Ala Gly Val Ser Cys Thr
1               5                   10

<210> SEQ ID NO 44
<211> LENGTH: 15
<212> TYPE: PRT
<213> ORGANISM: Homo sapiens

<400> SEQUENCE: 44

Met Asp Pro Asn Cys Ser Cys Ala Ala Ala Gly Val Ser Cys Thr
1               5                   10                  15

<210> SEQ ID NO 45
<211> LENGTH: 14
<212> TYPE: PRT
<213> ORGANISM: Homo sapiens

<400> SEQUENCE: 45

Met Asp Pro Asn Cys Ser Cys Ser Pro Val Gly Ser Cys Ala
1               5                   10

<210> SEQ ID NO 46
<211> LENGTH: 14
<212> TYPE: PRT
<213> ORGANISM: Homo sapiens

<400> SEQUENCE: 46

Met Asp Pro Asn Cys Ser Cys Ala Thr Gly Gly Ser Cys Ser
1               5                   10

<210> SEQ ID NO 47
<211> LENGTH: 14
<212> TYPE: PRT
<213> ORGANISM: Homo sapiens

<400> SEQUENCE: 47

Met Asp Pro Asn Cys Ser Cys Asp Pro Val Gly Ser Cys Ala
1               5                   10
```

```
<210> SEQ ID NO 48
<211> LENGTH: 14
<212> TYPE: PRT
<213> ORGANISM: Homo sapiens

<400> SEQUENCE: 48

Met Asp Pro Asn Cys Ser Cys Ala Ala Gly Asp Ser Cys Thr
1               5                   10

<210> SEQ ID NO 49
<211> LENGTH: 15
<212> TYPE: PRT
<213> ORGANISM: Homo sapiens

<400> SEQUENCE: 49

Met Asp Pro Glu Thr Cys Pro Cys Pro Ser Gly Gly Ser Cys Thr
1               5                   10                  15

<210> SEQ ID NO 50
<211> LENGTH: 15
<212> TYPE: PRT
<213> ORGANISM: Homo sapiens

<400> SEQUENCE: 50

Met Asp Pro Arg Glu Cys Val Cys Met Ser Gly Gly Ile Cys Met
1               5                   10                  15

<210> SEQ ID NO 51
<211> LENGTH: 14
<212> TYPE: PRT
<213> ORGANISM: Homo sapiens

<400> SEQUENCE: 51

Cys Thr Gly Ser Cys Lys Cys Lys Glu Cys Lys Cys Asn Ser
1               5                   10

<210> SEQ ID NO 52
<211> LENGTH: 14
<212> TYPE: PRT
<213> ORGANISM: Homo sapiens

<400> SEQUENCE: 52

Cys Ala Gly Ser Cys Lys Cys Lys Glu Cys Lys Cys Thr Ser
1               5                   10

<210> SEQ ID NO 53
<211> LENGTH: 14
<212> TYPE: PRT
<213> ORGANISM: Homo sapiens

<400> SEQUENCE: 53

Cys Ala Gly Ser Cys Lys Cys Lys Glu Cys Lys Cys Thr Ser
1               5                   10

<210> SEQ ID NO 54
<211> LENGTH: 14
<212> TYPE: PRT
<213> ORGANISM: Homo sapiens

<400> SEQUENCE: 54

Cys Ala Gly Ser Cys Lys Cys Lys Glu Cys Lys Cys Thr Ser
1               5                   10
```

```
<210> SEQ ID NO 55
<211> LENGTH: 14
<212> TYPE: PRT
<213> ORGANISM: Homo sapiens

<400> SEQUENCE: 55

Cys Ala Ser Ser Cys Lys Cys Lys Glu Cys Lys Cys Thr Ser
1               5                   10

<210> SEQ ID NO 56
<211> LENGTH: 14
<212> TYPE: PRT
<213> ORGANISM: Homo sapiens

<400> SEQUENCE: 56

Cys Ala Gly Ser Cys Lys Cys Lys Lys Cys Lys Cys Thr Ser
1               5                   10

<210> SEQ ID NO 57
<211> LENGTH: 14
<212> TYPE: PRT
<213> ORGANISM: Homo sapiens

<400> SEQUENCE: 57

Cys Ala Gly Ser Cys Lys Cys Lys Glu Cys Lys Cys Thr Ser
1               5                   10

<210> SEQ ID NO 58
<211> LENGTH: 14
<212> TYPE: PRT
<213> ORGANISM: Homo sapiens

<400> SEQUENCE: 58

Cys Ala Ser Ser Cys Lys Cys Lys Glu Cys Lys Cys Thr Ser
1               5                   10

<210> SEQ ID NO 59
<211> LENGTH: 14
<212> TYPE: PRT
<213> ORGANISM: Homo sapiens

<400> SEQUENCE: 59

Cys Ala Gly Ser Cys Lys Cys Lys Glu Cys Lys Cys Thr Ser
1               5                   10

<210> SEQ ID NO 60
<211> LENGTH: 14
<212> TYPE: PRT
<213> ORGANISM: Homo sapiens

<400> SEQUENCE: 60

Cys Ala Ser Ser Cys Lys Cys Lys Glu Cys Lys Cys Thr Ser
1               5                   10

<210> SEQ ID NO 61
<211> LENGTH: 14
<212> TYPE: PRT
<213> ORGANISM: Homo sapiens

<400> SEQUENCE: 61

Cys Ala Gly Ser Cys Lys Cys Lys Glu Cys Lys Cys Thr Ser
1               5                   10
```

```
<210> SEQ ID NO 62
<211> LENGTH: 14
<212> TYPE: PRT
<213> ORGANISM: Homo sapiens

<400> SEQUENCE: 62

Cys Ala Gly Ser Cys Lys Cys Lys Glu Cys Lys Cys Thr Ser
1               5                   10

<210> SEQ ID NO 63
<211> LENGTH: 14
<212> TYPE: PRT
<213> ORGANISM: Homo sapiens

<400> SEQUENCE: 63

Cys Ala Asp Ser Cys Lys Cys Glu Gly Cys Lys Cys Thr Ser
1               5                   10

<210> SEQ ID NO 64
<211> LENGTH: 14
<212> TYPE: PRT
<213> ORGANISM: Homo sapiens

<400> SEQUENCE: 64

Cys Gly Asp Asn Cys Lys Cys Thr Thr Cys Asn Cys Lys Thr
1               5                   10
```